US009101451B2

(12) United States Patent
Chugunov

(10) Patent No.: US 9,101,451 B2
(45) Date of Patent: Aug. 11, 2015

(54) METHOD FOR CORRECTING PATHOLOGICAL CONFIGURATIONS OF SEGMENTS OF THE LOWER EXTREMITIES AND DEVICE FOR REALIZING SAME

(75) Inventor: Vitaly Viktorovich Chugunov, Moscow (RU)

(73) Assignee: Zakrytoe Aktsionernoe Obschestvo Nauchno-Proizvodstvenny Tsentr "Ogonek", Moscow (RU)

( * ) Notice: Subject to any disclaimer, the term of this patent is extended or adjusted under 35 U.S.C. 154(b) by 388 days.

(21) Appl. No.: 13/515,855
(22) PCT Filed: Dec. 10, 2010
(86) PCT No.: PCT/RU2010/000746
§ 371 (c)(1), (2), (4) Date: Jun. 14, 2012
(87) PCT Pub. No.: WO2011/075003
PCT Pub. Date: Jun. 23, 2011

(65) Prior Publication Data
US 2012/0259259 A1 Oct. 11, 2012

(30) Foreign Application Priority Data

Dec. 15, 2009 (EA) .................................. 201000171
Nov. 12, 2010 (EA) .................................. 201001788
Nov. 26, 2010 (EA) .................................. 201100041

(51) Int. Cl.
*A61F 5/00* (2006.01)
*A61F 5/01* (2006.01)

(52) U.S. Cl.
CPC ............. *A61F 5/0102* (2013.01); *A61F 5/0123* (2013.01); *A61F 5/0127* (2013.01); *A61F 5/0193* (2013.01)

(58) Field of Classification Search
CPC ... A61F 5/0102; A61F 5/0123; A61F 5/0127; A61F 5/0193
USPC ............................. 602/5, 16, 23–28; 128/882
See application file for complete search history.

(56) References Cited

U.S. PATENT DOCUMENTS 5,362,305 A 11/1994 Varn 5,658,242 A 8/1997 McKay et al.
(Continued)

FOREIGN PATENT DOCUMENTS

FR  2 802 801     6/2001
GB  2 301 776    12/1996
(Continued)

OTHER PUBLICATIONS

International Search Report of PCT/RU2010/000746, date of mailing May 5, 2011.

(Continued)

*Primary Examiner* — Michael Brown
(74) *Attorney, Agent, or Firm* — Collard & Roe, P.C.

(57) ABSTRACT

The invention relates to a method for the step-by-step correction of the position of the longitudinal axes of segments of the lower extremities in the horizontal and/or frontal and/or sagittal planes, that comprises the simultaneous dosed correction of the imbalance of forces in the muscles supporting the corresponding joints, the reduction of the pathological configurations of the segments, and the fixation of corrected segments using at least one module of a modular exoskeleton capable of individual adjustment for bringing, during each step, the position of the longitudinal axis of each segment closer to the physiologically correct position, and for permitting movements about the corrected rotation axes of the joints within a predetermined range defined by the modular exoskeleton. The proposed device for correcting pathological configurations of segments of the lower extremities comprises a modular exoskeleton, the modules of which can be used independently or in various combinations. The modular exoskeleton comprises at least one adjustable pelvis belt (1, 47), at least one means (3, 51) for holding the thigh in a given position, at least one means (4, 89) for rotating the tibia, at least one means (5, 121) for holding the tibia in a given position, at least one means (6, 130) for correcting the position of the foot and the movement range thereof at the foot-tibia joint, at least one means (7, 146) for accommodating the foot, and a set of fixation members each in the form of a cylindrical rod (8, 9, 10, 11, 37, 52, 83, 90, 124, 141, 142) capable of linear positioning movement and/or rotation and/or free linear movement.

59 Claims, 21 Drawing Sheets

(56) References Cited

U.S. PATENT DOCUMENTS

| | | | |
|---|---|---|---|
| 6,540,703 B1 | 4/2003 | Lerman | |
| 2007/0123997 A1* | 5/2007 | Herr et al. | 623/27 |
| 2008/0234608 A1* | 9/2008 | Sankai | 601/5 |
| 2010/0036302 A1* | 2/2010 | Shimada et al. | 602/16 |
| 2010/0094185 A1* | 4/2010 | Amundson et al. | 602/16 |

FOREIGN PATENT DOCUMENTS

| | | |
|---|---|---|
| JP | 2006-087478 | 4/2006 |
| RU | 2 241 500 | 12/2004 |
| RU | 2 307 640 C1 | 10/2007 |
| RU | 2 309 709 | 11/2007 |

OTHER PUBLICATIONS

Ortopediya. Natsionalnoe rukovodstvo, M. "GEOTAR-Media" 2008, p. 152, paragraph 8, p. 153, paragraph 1, 2, 4, drawings 6-6, 6-7, 6-8. (ISR) (title page and pp. 152-153 enclosed) (With concise explanation).

Culik, J. et al. "Biomechanics of leg deformity treatment", J. Musculoskelet Neuronal Interact 2008; 8(1): pp. 58-63. (ISR).

* cited by examiner

METHOD FOR CORRECTING PATHOLOGICAL CONFIGURATIONS OF SEGMENTS OF THE LOWER EXTREMITIES AND DEVICE FOR REALIZING SAME

CROSS REFERENCE TO RELATED APPLICATIONS

This application is the National Stage of PCT/RU2010/000746 filed on Dec. 10, 2010, which claims priority under 35 U.S.C. § 119 of Eurasian Patent Organization No. 201000171 filed on Dec. 15, 2009, Eurasian Patent Organization No. 201001788 filed on Nov. 12, 2010, and Eurasian Patent Organization No. 201100041, filed on Nov. 26, 2010, the disclosures of which are incorporated by references. The international application under PCT article 21 (2) was not published in English.

FIELD OF THE INVENTION

The present invention is in the field of medicine, specifically traumatology, orthopedics, and neurology, and more specifically—methods for correcting pathological configurations of segments of the lower extremities and devices for realizing same.

At the present time, due to worsening of the ecological environment, the impact of adverse factors on the population—including pregnant women—is rising and, as a consequence, propensity of the next generation to inherited pathologies is also rising. The issue of correcting pathological configurations of segments of the lower extremities, including those in young children, is rather pressing, as there is a rising worldwide incidence of said pathologies.

By segments of the lower extremities we mean various regions of the musculoskeletal system of the lower extremities of the human body, such as the thigh segment, the tibia segment, and the foot segment.

PRIOR ART

Prior art knows various methods and devices for restoration of the locomotive function of various regions of the musculoskeletal system, including those employing correction of pathological configurations of segments of the lower extremities. Therein, at least three directions are evident.

The well-known first direction comprises the execution of said correction by means of the step-by-step application of gypsum bandages onto segments of the lower extremities, to eliminate pathological configurations of the thigh, tibia, ankle, foot, and the like.

However, the utility of said method is limited and it can be used, as a rule, in children, primarily those of young age.

Moreover, utilization of said method assumes that the user will stay, for a long period, in a position that, throughout the correction process, precludes free movement, which leads to partial loss of motor skills and hypotrophy of muscles of the pelvic girdle and the lower extremities.

The second direction comprises the execution of said correction with the aid of various devices comprising exercise machines, by making use of exercises that reduce pathological configurations of segments of the lower extremities.

For example, prior art knows exercise machine "Lotus," and the method for correcting pathological changes in the patient's locomotive apparatus using said machine.

The user is placed in said exercise machine in a sitting position "Turkish-style," his/her back flush with vertical support. Tibias of the lower extremities are held in a given position using a fixation module, knees—using a small table placed onto them, and the back—using vertical support. The user spends two to three hours a day in said position.

The use of said method and device allows correction of pathological configurations of segments of the lower extremities. However, this correction can only be achieved after many years of physical exercise, and only to an insignificant extent. Moreover, the utility of said method and device is limited inasmuch as they can be used in adults and older children, but cannot be used for correction of pathological configurations of segments of the lower extremities in younger children, including those suffering from infantile cerebral palsy (ICP).

Further, fixation of the user in said exercise machine limits free movements of the user, whereas holding the lower extremities in a given position precludes the development of motor skills and is not conducive to unassisted movement of the user.

The third direction comprises the execution of said correction, to an insignificant extent, using various devices that promote free movement of the user, despite the presence of pathological configurations of segments of the lower extremities.

Said devices are put on the user, by means of which a so-called "exoskeleton" is created on the user that protects muscles and the capsule-ligament apparatus of the joints in the lower extremities, and allows the user to move unassisted. During said movement, an insignificant correction of pathological configurations of segments of the lower extremities takes place.

In patent application GB 2 301 776 A, there is a description of a method and device for facilitation of walking that is equipped with a means of control. Prior art knows a device comprising exoskeleton that consists of an outer carcass to be worn around the body and the lower limbs of the user, and a means of control to direct the device. The outer carcass, it its turn, comprises a pelvic section, a thigh section, a thigh joint section, a knee joint section, a tibia section, an ankle section, and a foot section. Said sections are interconnected via hinges and sliders, and operated using a joystick.

When the joystick is moved by the user's hands, signals are transmitted to certain sliders that bring into motion certain elements of the exoskeleton, thus facilitating the movement of the user. Following long-term use of the exoskeleton, an insignificant correction of pathological configurations of segments of the lower extremities takes place.

However, said device comprises a complicated construction, and is custom-produced for a given user as the thigh and tibia sections have fixed lengths which precludes one—if necessary—from changing this device's linear dimension. Thus, the utility of said device is limited.

Moreover, said device may only be used as a single construction. In the event when it is not medically necessary to assist the movement of all regions of the lower extremities, utilization of such a device is not reasonable.

In U.S. Pat. No. 5,658,242 there is a description of a method and device for facilitation of locomotive functions of the lower extremities, which afford a possibility of insignificant correction of pathological configurations of segments of the lower extremities.

Said device comprises a complex, single construction and consists of a supporting waist band, talocrural supporting bands, and supporting bands for the thighs. Said bands are interconnected by rigid ties that feature a hinge connection at each knee joint. This device comprises a rigid exoskeleton manufactured in accordance with the specific dimensions of a given user, and it has large overall dimensions and a complex structure.

Utilization of said device and method allows unburdening of the supporting elements and muscles of the lower extremities, which allows the user to move without assistance.

However, the utility of said method and device is limited as they can be used to move adults and older children, but cannot be used for correction of pathological configurations of segments of the lower extremities in younger children, including those suffering from infantile cerebral palsy, since the device is good only for individual use due to the fact that it is manufactured in accordance with the specific dimensions of a given user without the possibility of correcting the device while applying this method. This precludes the possibility of using said device and method in children whose body dimensions change substantially within a short time period. Moreover, use of said device leads to weakening and hypotrophy of muscles of the lower extremities.

Prior art knows device and method to facilitate walking (JP 2006 087478), which afford the possibility of a very insignificant correction of pathological configurations of segments of the lower extremities. Said device features an adjustable pelvic belt positioned around the pelvic area of the user, on each side of which—along the corresponding lower extremity of the user—there is a means for rotating the thigh joint, a means for holding the thigh in a given position, a means for rotating the tibia, a means for holding the tibia in a given position, a means for correcting the position of the foot and the movement range thereof in the talocrural joint, and a means for accommodating the foot. Said devices are interconnected via connecting elements comprising flat rods.

The known method and device are meant to ease the movement of users lacking peripheral innervations of the lower extremities.

The pelvic belt of the known device ensures the positioning of the apparatus on the body of the user; moreover, the means of rotating the thigh joint connected to the pelvic belt comprises a flat thigh hinge that allows carrying out the movement of the thigh in the sagittal plane only. To achieve a forced movement of the thigh, there is a first electric drive located in the zone of the thigh hinge.

The means of holding the thigh in a given position comprise a flat rod held on the user's thigh by two thigh cuffs and firmly connected to the thigh hinge and the means for rotating the tibia, executed as a flat hinge (knee hinge). There is a second electric drive located in the zone of the knee hinge that ensures rotation of the knee hinge and, respectively, rotation of the tibia in the sagittal plane.

The means of holding the tibia in a given position is executed analogously to the means of holding the thigh: it also comprises a flat rod held on the user's tibia using a calf cuff and firmly connected to the knee hinge.

In the known device, the means for correcting the position of the foot and the movement range thereof in the talocrural joint is executed as a flat hinge (talocrural hinge), and it ensures back-and-forth movement of the foot in the sagittal plane. The means for accommodating the foot, executed as a lightweight boot, is firmly connected to the means for correcting the position of the foot and the movement range thereof.

Said device comprises a single exoskeleton construction providing for simultaneous use of all structural and functional parts. The respective electric drives of the thigh region and the knee joint govern the operational mechanisms that function for the purpose of unburdening the walking process of users lacking peripheral innervations of the lower extremities.

The utility of the known device is limited and it cannot be used by individuals with hip dislocations and subluxations because the pelvic belt of the known device only allows positioning of the device on the user's body, and does not allow centering the femoral head in the hip socket. The lack of ability to center the femoral head, in its turn, does not allow applying an adequate load onto the entire surface of the user's lower extremity.

Using the known device, it is not possible to carry out correction of the rotation axis of the knee joint because the flat knee hinge used therein does not allow correction of the tibia's position relative to the thigh when the position of the tibia is abnormal.

Moreover, the known device does not allow adaptation to the user's anatomical characteristics because it is not possible to change the configuration of the flat connecting rods that takes into account, for example, the shape of the tibia or the thigh.

Further, said device features a complex construction, including hinge connections containing moving and rotating parts that are in direct proximity to the user's body, which practically precludes the use of this device in children, including younger children.

DESCRIPTION OF THE INVENTION

At the foundation of the invention, there lies the goal to create a method for correcting pathological configurations of segments of the lower extremities and device for realizing same, so that the method's specific techniques and simplified execution of the device would allow simultaneously—or in a given combination—carrying out correction of pathological configurations of segments of the lower extremities in the horizontal and/or frontal and/or sagittal planes while ensuring a possibility of movement around the corrected biomechanical rotation axes of the hip, knee, and talocrural joints, and also broaden the possibilities of correcting pathological configurations of segments of the lower extremities and ensure a possibility of using the invention in adults and children of various ages, including young children, ensure a possibility of free movement of the user during the correction process, and simultaneous step-by-step elimination of various singular or combinatorial pathological configurations of segments of the lower extremities.

This goal is achieved by creating a method for correcting pathological configurations of segments of the lower extremities comprising the correction of pathological configurations of the segments of at least one lower extremity using an orthopedic device in which, as per the invention, said correction comprises the step-by-step correction of the position of the longitudinal axes of said segments in the horizontal and/or frontal and/or sagittal planes by means of the simultaneous dosed correction of the imbalance of forces in the muscles supporting the corresponding joints, reduction of pathological configurations of said segments, and subsequent fixation of the segments in the correct position at each step using an orthopedic device comprising at least one module of a modular exoskeleton executed so that it is capable of individual adjustment for bringing, during each step, the position of the longitudinal axis of each pathologically configured segment closer to the physiologically correct position, whereby fixation of said segments in the corrected position at each step is achieved while permitting movements in the corresponding joints around the corrected rotation axes of these joints within a range predetermined by said modular exoskeleton, and the stereotype of the user's movements in the corresponding joints is thus brought closer to the physiologically correct movement stereotype.

The technical outcome comprises improved support ability of the lower extremities and correction of a pathological pose and movement stereotype in young children, teenagers, and adults suffering from spastic or atonic palsy of the lower extremities of various etiology, diseases of the musculoskeletal system including metabolic disorders, or any other diseases and conditions leading to singular or combinatorial pathological configurations of segments of the lower extremities.

This allows broadening of the proposed method's field of use and ensures a possibility to use the proposed method in adults and children of various ages, including young children, while ensuring free movement of the user during the correction process with the preservation of the ability of active movements in the large joints of the lower extremities (hip, knee, and talocrural) and the simultaneous step-by-step elimination of various singular or combinatorial pathological configurations of segments of the lower extremities.

Moreover, the proposed method can be used for correcting pathological configurations of single segments of the lower extremities, which makes it possible to use not the entire exoskeleton, but only its separate modules.

It is reasonable to reduce pathological configurations of segments such as hip adduction in the corresponding hip joint in a step-by-step manner, wherein the correction of said configurations is carried out by the simultaneous dosed stretching of hip adductors and dosed correction of the position of the femoral head in the socket of the corresponding hip joint by hip abduction in the frontal plane, as well as the subsequent fixation of the corrected position using the first module of the exoskeleton, which allows movement in the corresponding hip joint in the horizontal, frontal, and sagittal planes within a range predetermined by said first module.

In the case of pathological inner rotational configuration of the hip it is desirable to conduct, simultaneously with the dosed hip abduction in the frontal plane, its dosed outer rotation in the horizontal plane.

It is favorable to reduce pathological configurations of segments such as inner rotation of the lower extremity in a step-by-step manner, wherein the correction of said configurations is carried out by the simultaneous dosed correction of the imbalance of forces in the muscles supporting the corresponding hip joint, and outer rotation of the lower extremity in the corresponding hip joint, as well as the subsequent fixation of the corrected configuration using the first and the second modules of the exoskeleton, which allows movement in the corresponding hip and knee joints in the horizontal plane within a range predetermined by said first and second modules.

It is possible to reduce pathological configurations of segments such as recurvation of the tibia in the knee joint, wherein the correction of said configurations is carried out by the dosed limitation of tibia extension in the knee joint in the sagittal plane during the support period upon locomotion and fixation of the corrected configuration using the second module of the exoskeleton, which allows tibia flexion and extension in the knee joint in the sagittal plane within a range predetermined by said second module.

It is useful to reduce pathological configurations of segments such as tibia flexion in the knee joint in a step-by-step fashion, wherein the correction of said configurations is carried out by the simultaneous dosed correction of the imbalance of forces in the muscles supporting the knee joint, and limitation of flexion of the tibia in the knee joint in the sagittal plane during the support period upon locomotion and the subsequent fixation of the corrected configuration using the spring-assisted second module of the exoskeleton, which allows tibia flexion and extension in the knee joint within a range predetermined by said second module.

It is preferable to reduce, in a step-by-step manner, pathological configurations of segments such as varus or valgus positioning of the tibia in the knee joint, wherein the correction of said configurations is carried out by the simultaneous dosed correction of the imbalance of forces in the muscles supporting the knee joint and correction of the tibia's position in the frontal plane, as well as the subsequent fixation of the corrected configuration using the second module of the exoskeleton, which allows tibia flexion and extension in the knee joint in the sagittal plane within a range predetermined by said second module.

It is convenient to reduce, in a step-by-step manner, pathological configurations of segments such as foot adduction or abduction in the talocrural joint, wherein the correction of said configurations is carried out by the simultaneous dosed correction of the imbalance of forces in the muscles supporting the talocrural joint and the corresponding abduction or adduction of the foot in the horizontal plane, as well as the subsequent fixation of the corrected configuration of the foot using the third module of the exoskeleton, which allows plantar flexion and dorsiflexion of the foot in the talocrural joint in the sagittal plane within a range predetermined by said third module.

It is reasonable to reduce, in a step-by-step manner, pathological configurations of segments such as varus or valgus positioning of the foot in the talocrural joint, wherein the correction of said configurations is carried out by the simultaneous dosed correction of the imbalance of forces in the muscles of the calf and changing the position of the foot in the talocrural joint in the frontal plane, as well as the subsequent fixation of the corrected configuration of the foot using the third module of the exoskeleton and individual correcting inserts installed on the inner or the outer surface of the device for accommodating the foot of the exoskeleton, which allows plantar flexion and dorsiflexion of the foot in the talocrural joint in the sagittal plane within a range predetermined by said third module.

It is preferable to reduce, in a step-by-step manner, pathological configurations of segments such as dropping of the foot in the talocrural joint, wherein the correction of said configurations is carried out by limiting the possibility of plantar flexion of the foot in the sagittal plane and the subsequent fixation of the corrected configuration of the foot using the third module of the exoskeleton, which allows dorsiflexion of the foot in the talocrural joint in the sagittal plane within a range predetermined by said third module.

It is favorable to reduce, in a step-by-step manner, pathological configurations of segments such as equine positioning of the foot in the talocrural joint, wherein the correction of said configurations is carried out by the simultaneous dosed stretching of the triceps muscle of the corresponding calf and limiting plantar flexion of the foot in the sagittal plane, as well as the subsequent fixation of the corrected configuration of the foot using the third module of the exoskeleton, which allows dorsiflexion of the foot in the talocrural joint in the sagittal plane within a range predetermined by said third module.

It is reasonable to reduce, in a step-by-step manner, said pathological configurations of segments of the two lower extremities whose correction is carried out independently for each lower extremity without cross-effect.

It is useful, at each step of the correction, to bring the position of the longitudinal axis of said pathologically configured segment to the physiologically correct position, wherein said correction is carried out to the extent that precludes painful sensations for the user.

It is possible to carry out said correction until the physiologically correct position of the longitudinal axis of the user's corresponding lower extremity is achieved while standing.

It is preferable to perform, between the steps of said correction, active dynamic exercises to eliminate functional deficiency in the corresponding muscles and/or exert influences on the user that are chosen from a set comprising manual, device-mediated, physical therapy, and medicinal options, alone or in combination.

Use of the proposed method improves support ability of the lower extremities and correction of a pathological pose and locomotive stereotype in young children, teenagers, and adults suffering from spastic or atonic palsy of the lower extremities of various etiology, diseases of the musculoskeletal system including metabolic disorders, or any other diseases and conditions leading to singular or combinatorial pathological configurations of segments of the lower extremities.

This broadens the field of use of the proposed method and ensures a possibility to use the proposed method in adults and children of various ages, including young children, while allowing free movement of the user during the correction process with preservation of the possibility of active movements in the large joints of the lower extremities (hip, knee, and talocrural) within the corrected movement range.

The stated goal is also achieved by creating a device for correcting pathological configurations of segments of the lower extremities, comprising an adjustable pelvic belt positioned around the pelvic area of the user, at least one means for holding the thigh in a given position, at least one means for rotating the tibia, at least one means for holding the tibia in a given position, at least one means for correcting the position of the foot and the movement range thereof in the talocrural joint, at least one means for accommodating the foot, and a set of connecting elements in which, as per the invention, said adjustable pelvic belt is executed so that the head of at least one femur can be centered, said means for holding the thigh in a given position is executed to allow positioning rotation in the horizontal plane, said means for rotating the tibia is executed so that the position of the rotation axis of the knee joint can be corrected in the frontal and horizontal planes, said means for holding the tibia in a given position is executed so that the foot can rotate in the horizontal plane, each connecting element in said set of connecting elements essentially comprises a cylindrical rod executed to allow for linear positioning movement and/or rotation and/or free linear movement, whereby said adjustable pelvic belt and at least one said means for holding the thigh in a given position are connected via the first rod executed to allow rotation and free linear movement, and comprise the first module executed to allow positioning rotation in the horizontal plane and hip rotation in the static position and at movement, at least one said means of holding the thigh in a given position, at least one said means for rotating the tibia and at least one said means for holding the tibia in a given position connected, respectively, via the second and third rods and comprise the second module, wherein said second rod is executed to allow rotation and linear positioning movement, said third rod is executed to allow linear positioning movement, and said second module is executed so that the position of the tibia can be changed via inner or outer rotation of the tibia in the horizontal plane and the position of the tibia in the frontal plane can be corrected, at least one said means for holding the tibia in a given position, and at least one said means for correcting the position of the foot and the movement range thereof in the talocrural joint are connected via the fourth rod executed to allow linear positioning movement and comprise the third module executed so that the position of the tibia and the foot can be changed via outer or inner rotation of the tibia and the foot in the horizontal plane; said first, second, and third modules are executed to allow autonomous use or use in a given combination depending on the type of pathological configurations of segments of the user's lower extremities.

The technical outcome of claimed invention is the ability to correct the configuration of the positions of the rotation axes of the hip, knee, and talocrural joints in the horizontal, frontal, and sagittal planes.

The device being patented can be used for functional correction of pathological configurations of the hip, the tibia, and the foot, such as inner rotation of the axis of a lower extremity, inner rotation of the hip, hip adduction, varus or valgus positioning of the tibia, varus or valgus positioning of the foot, equine positioning of the foot, dropping of the front region of foot, adduction or abduction of the foot in a setting of various clinical forms of infantile cerebral palsy, in a setting of a partial damage of the spinal cord, as well as damage of peripheral nerves and other diseases of adults and children leading to pathological configurations of segments of the lower extremities.

Due to the modular execution of the device, it is possible to simultaneously correct all segments of the lower extremities including a situation in which the user presents with various combinations of pathological configurations of the thigh, tibia, and foot of one or both lower extremities.

The construction of the proposed device is fairly uncomplicated and comprises simplified construction units, which is particularly important when the device is to be used in young children. Connecting elements comprising cylindrical rods allow changing the device's entire length, and also perform rotation and free linear movements of its parts. This allows precise adaptation of the device for a given user, which is particularly important for children during their brisk growth.

It is reasonable that said adjustable pelvic belt contains a supporting plate on which a base is mounted that is oriented along the pelvic belt, on each of the opposing sides of which there is a means for centering the femoral head comprising a flange featuring a semi-spherical concavity, a removable lid firmly connected to said flange and featuring an inverse semi-spherical concavity, and a sphere shaped hinge firmly secured in said concavities with a possibility of free positional rotation and featuring the first through channel in which, with a possibility of free movement, the first end of said first rod is secured.

The device being patented ensures centering of the femoral head in the hip socket with the simultaneous correction of the longitudinal axis of the lower extremity. The claimed construction of the means of centering the femoral head allows for hip abduction in static positions ("sitting," "standing") as well as during locomotion.

Said means of centering the femoral head is tuned so that a distinct range of hip abduction is ensured at various body positions ("sitting," "standing"), and during locomotion. Such tuning is achieved due to the possibility of free positional rotation of the spherical hinge in the frontal and horizontal planes, and its fixation in a given position corresponding to the pathology of a given user.

It is useful to execute said means for holding the thigh in a given position so that it comprises the first and the second parts, mounted with a possibility of free rotation of one relative to the other in the sagittal plane and with a possibility of positioning rotation in the horizontal plane, wherein the device would have an adjustable thigh cuff on which, with a possibility of rotation in the sagittal plane, the first part of said means for holding the thigh in a given position is mounted having the second through channel in which, with a possibility of rotation and linear positioning movement, the first end of said second rod is secured, and the second part of said means for holding the thigh in a given position has the third through channel in which, with a possibility of free linear movement, the second end of said first rod is secured.

It is preferable for said means for holding the thigh in a given position to contain an axle connecting said adjustable thigh cuff with said first and second parts of the means for holding the thigh in a given position, wherein the ends of this axle are fastened with a possibility of free rotation on said adjustable thigh cuff and said second part of said means for holding the thigh in a given position.

It is possible for said means for rotating the tibia to comprise two parts, assembled to allow positioning rotation of one relative to the other in the frontal and horizontal planes, wherein the first part of said means for rotating the tibia has the fourth through channel in which, with a possibility of linear positioning movement, the second end of said second rod is secured, and the second part of said means for rotating the tibia features a slit in which, on axle, a knee hinge is placed executed with a possibility of limiting flexion and extension of the tibia in the sagittal plane and having a socket in which the first end of said third rod is firmly secured.

It is useful to have said knee hinge contain a needle bearing, the axle of which is secured, with its ends, at the opposing sides of said second part of the means for rotating the tibia, and the region of said slit in the second part features a stop limiting the turning of said knee hinge in the sagittal plane.

The presence of a stop that limits rotation of the knee hinge unit in the sagittal plane prevents tibia hyperextension.

There are constructive grounds for said means for rotating the tibia to contain an axle, one end of which is firmly secured at said first part of the means for rotating the knee joint, and the other end of said axle is placed in said second part of the means for rotating the tibia with a possibility of rotation of said second part relative to its first part.

The described means for rotating the tibia (i.e. correcting the position of the rotation axis of the knee joint) allows correction of the position of the tibia in the horizontal and frontal planes while simultaneously performing the required flexion-extension repeating the movement of the tibia during walking.

It is preferable for said means for holding the tibia in a given position to contain an adjustable calf cuff and a base having the fifth and sixth through channels, in which, with a possibility of linear positioning movement, the second end of said third rod and the first end of said fourth rod are secured, respectively, wherein said base has an axle on which, with a possibility of rotation in the sagittal plane, said adjustable calf cuff is secured.

It is reasonable to execute the means for holding the tibia in a given position with one adjustable cuff positioned in midcalf when the length of the tibia is not great and when the volume of the calf does not change substantially along its length. In such a case, the cuff is safely secured on the calf and does not cause inconvenience when the apparatus is in use.

If there is a substantial change in the volume of the calf along its length, it is favorable to have said means for holding the tibia in a given position contain the first and second adjustable calf cuffs and the first and second bases, each of which has the seventh and eighth through channels, wherein the device contains an intermediate rod and said seventh through channel of said first base has a firmly secured second end of said third rod, whereas said eighth through channel of said first base has, with a possibility of linear positioning movement, the secured first end of said intermediate rod, and in said seventh and eighth through channels of said second base, with a possibility of positioning linear movement, the second end of said intermediate rod and the first end of said fourth rod are secured, respectively, wherein each said base has an axle on which, with a possibility of rotation in the sagittal plane, the corresponding said adjustable calf cuff is secured.

It is useful to have said intermediate rod executed to be bent according to the shape of the user's tibia.

The option of executing the apparatus with two calf cuffs, one of which is placed in the upper part of the calf under the knee and the other—in the lower part, closer to the talocrural joint, ensures a more reliable function of the means for holding the tibia in the given position, excluding tilts and poor fit to the tibia.

It is desirable to have said means for correcting the position of the foot and the movement range thereof in the talocrural joint contain a talocrural hinge having a hollow body in which a tip is placed, the first end of which has a firmly secured second end of said fourth rod, and the second end of said tip is secured in said hollow body on the axle of said talocrural hinge with a possibility of rotation in the sagittal plane.

It is preferable to have the device contain a connecting plate with its one end secured on said axle of said talocrural hinge with a possibility of rotation in the sagittal plane and its other end firmly attached to said means for accommodating the foot.

It is convenient to have the configuration of said connecting plate conform to the anatomical specifications of the user's foot.

It is reasonable to place, in said hollow body of the talocrural hinge of said means for correcting the position of the foot and the movement range thereof in the talocrural joint, at least one spring element executed with a possibility to limit rotation of the foot in the sagittal plane.

It is possible to have said means for accommodating the foot contain a boot and at least one fastening element to hold the foot in a given position.

Means for correcting the position of the foot and the movement range in the talocrural joint, executed as described above, ensures a possibility to correct pathological configurations of the foot, and it is reliable and user-friendly.

Presence of spring elements ensures smooth movement of the talocrural joint, which makes it easier to use the device.

It is favorable to have the device contain a means for extending the knee joint secured in the zone of placement of the corresponding ends of said second and third rods.

It is preferable to have said means for extending the knee joint have at least one spring, one end of which is secured on said second part of the means for rotating the tibia and the other—on said first end of the third rod.

It is desirable to have said means for extending the knee joint contain at least one mover placed in the zone where the corresponding ends of said second and third rods are located.

It is reasonable to have the device contain a mover fastened on said adjustable pelvic belt in the zone where said means for centering the femoral head is located.

It is preferable to have said adjustable pelvic belt contain a base near each of the opposing ends of which a corresponding landing place is located containing the first ring-like ridge surface, on which the corresponding means for centering the femoral head is placed that is fastened on the corresponding landing place with a possibility of positional rotation and contains a body on the surface of which, facing the base, there is the second ridge surface, and a bevel-edged nut positioned between said base and said body with a possibility of positioning rotation and having, on its butt-ends, the third and fourth ring-like ridge surfaces executed with a possibility of interlocking with said first and second ring-like ridge surfaces, respectively.

It is favorable for the device to have at least one adjustable thigh cuff executed with a possibility of a turn in the sagittal plane, on which, with a possibility of a positioning turn in the horizontal plane, a corresponding means for holding the thigh in a given position is fastened, and inside said body of the means for centering the femoral head there is the ninth through channel oriented along the base, in which the means for fastening the first end of said first connecting rod is secured, executed to allow free rotation and linear positioning movement of said first end of the first connecting rod, said second end of which is positioned in said means for holding the thigh in a given position.

It is useful to have said device for fastening said first end of the first rod contain the first and second hubs with the corresponding flanges positioned with a possibility of free rotation in said ninth through channel of said body of the means for centering the femoral head from the opposing sides, wherein the outer surface of said first end of the first rod and inner surfaces of said first and second hubs are threaded and form a threading connection to ensure linear positioning movement of said first end of the first rod.

It is possible for said first bevel-edged nut to be executed with a possibility of discrete positioning rotation, and there is a scale on the corresponding said landing place around said first ring-like ridged surface, the unit of which corresponds to a step of the discrete positioning rotation of said bevel-edged nut.

It is preferable to have the bevel angle of said bevel-edged nut be from 3 to 30°.

It is reasonable to have said means for centering the femoral head to contain the first flat spring placed between juxtaposed said surfaces of said base and bevel-edged nut, respectively, inside said first and third ring-like ridged surfaces.

It is preferable to have said means for centering the femoral head contain the second flat spring positioned between the juxtaposed said surfaces of the base and the bevel-edged nut, respectively, inside said second and fourth ring-like ridged surfaces.

It is favorable to have said means for holding the thigh in a given position contain a hollow body and a unit of fastening said means for holding the thigh in a given position to said adjustable thigh cuff, wherein said unit is fastened from one side of this hollow body partially inside of it with a possibility of rotating the thigh in a static position and during movement, and from the opposite side of said hollow body, with a possibility of linear movements, said second end of the first rod is positioned.

It is possible to have said unit of fastening said means for holding the thigh in a given position contain an insert fastened in said hollow body of the means for holding the thigh in a given position, and having a tailpiece protruding from this hollow body in which a ball bearing is placed having a stator and a rotor, executed with a possibility of rotation in the sagittal and horizontal planes.

It is useful for the device to have at least one unit of fastening the first end of said second rod positioned with a possibility of rotation in the horizontal plane and having the tenth through channel in which, with a possibility of linear positioning movement, said first end of the second rod is secured.

It is preferable for said means for rotating the tibia to contain a stepped body in the first step of which the second end of said second rod is fastened, that is executed with a possibility of positioning rotation in the frontal and horizontal planes, and in the second step of which a knee hinge is mounted that is executed with a possibility of limited rotation in the sagittal plane, and there is a unit of fastening the first end of said third rod connected to said knee hinge.

It is reasonable to have said knee hinge contain a base, a lid executed with a possibility of discrete positioning rotation and fixation in a given position, a spring with its one end fastened in said second step of stepped body and the other—in said lid of the knee hinge, and an axle whose one end is fastened in said second step of the stepped body and the other in said lid of the knee hinge.

It is desirable to have an insert positioned between said base of the knee hinge and said second step of the stepped body, executed with a possibility of limiting rotation of said knee hinge.

It is favorable to have said insert be C-shaped, and made of a resilient material.

It is possible to have said unit of fastening the first end of the third rod contain a collar fastened on said base of the knee hinge, and a lock executed with a possibility of entering inter-engagement with said lid of the knee hinge.

It is useful to have the device contain a clamping element grasping said collar and lock.

It is preferable to have said means for rotating the tibia contain a ridged pair executed with a possibility of limited rotation in the sagittal plane and comprising the first and second gears, each of which has a ridged crown and a rotation axle, the first and second side plates positioned from the butt-end of the ridged pair in which the first and second rotation axles are fastened that pass through said first and second gears, and the front and back stops fastened on one of said side plates, wherein said second end of the second rod is fastened in said first gear, and said first end of the third rod is fastened in said second gear.

It is reasonable to have said means for holding the tibia in a given position contain the first adjustable calf cuff on which, with a possibility of rotation in the sagittal plane, the first base is fastened, and the second adjustable calf cuff on which, with a possibility of rotation in the sagittal plane, the second base is fastened, wherein the device contains the first intermediate rod connecting said first and second adjustable calf cuffs.

It is desirable to have said means for correcting the position of the foot and the movement range thereof in the talocrural joint contain an outer talocrural hinge having a hollow body in which a tip is inserted on whose one end the second end of said fourth rod is fastened, and the other end of said tip is fastened on the axle of the outer talocrural hinge with a possibility of rotation in the sagittal plane, whereby the device contains a bent connecting plate with its one end fastened to said axle of the outer talocrural hinge with a possibility of rotation in the sagittal plane, and the other end fastened to said means for accommodating the foot.

It is favorable to have at least one resilient element installed in said hollow body of the means for correcting the position of the foot and the movement range thereof in the talocrural joint, executed with a possibility of limiting rotation of the foot in the sagittal plane.

It is possible to have said means for correcting the position of the foot and the movement range thereof in the talocrural joint contain an outer talocrural hinge, having an axle and a body in which the second end of said fourth rod is fastened, wherein the device contains a bent connecting plate that is spring-loaded to said body, with its one end fastened to said axle of the outer talocrural joint with a possibility of rotation in the sagittal plane, and the other end—to said means for accommodating the foot.

It is useful to have the device contain at least one second intermediate rod, and said means for correcting the position of the foot and the movement range thereof in the talocrural joint contain at least one inner talocrural hinge, whereby the first and second collars are placed onto said first and second adjustable calf cuffs from the inner surface of the calf with a possibility of rotation in the sagittal plane, and in the first collar, with a possibility of linear positioning movements, the first end of said second intermediate rod is fastened, the second end of which is passed through said second collar and connected to said inner talocrural hinge.

It is preferable to have said inner talocrural hinge have a hollow body in which a tip is installed, on one end of which said second end of the second intermediate rod is fastened, and the second end of the tip is fastened on the axle of said inner talocrural hinge with a possibility of rotation in the sagittal plane, whereby the device contains a bent connecting plate whose one end is fastened to the axle of said inner talocrural hinge with a possibility of rotation in the sagittal plane, and the other end is fastened to said means for accommodating the foot.

It is reasonable for said inner talocrural hinge to have a body in which said second end of the second intermediate rod is fastened, whereby the device contains a bent connecting plate spring-loaded to said body, with its one end fastened to the axle of said inner talocrural hinge with a possibility of rotation in the sagittal plane, and its other end fastened to said means for accommodating the foot.

It is preferable to have each said first rod be executed as a cylindrical pivot with a complex three-dimensional shape and having its first straight-line segment oriented along the rotation axis of said first rod, its second straight-line segment essentially oriented along the user's tibia, and its third curvilinear segment smoothly connecting said first straight-line segment and second straight-line segment.

The device being patented for correcting pathological configurations of segments of the lower extremities is unique in comparison to other devices of same utility, because it ensures high effectiveness of the outcomes due to the possibility to perform correction of the position of the longitudinal axes of segments of the lower extremities and the positions of rotation axes of the hip, knee, and talocrural joints. The device being patented can be adapted to a given user which facilitates the use of such a device. Lack of rotating or rubbing parts that are in contact with the user's body is also its unquestionable advantage.

Moreover, the use of the proposed device improves the support ability of the lower extremities and the correction of a pathological configuration and locomotive stereotype in children of young age, teenagers, and adults suffering from spastic or atonic palsy of the lower extremities of various etiology, diseases of the musculoskeletal system including metabolic disorders, or any other diseases and conditions leading to singular or combinatorial pathological configurations of segments of the lower extremities.

This broadens the field of use of the proposed device and ensures a possibility to use the proposed device in adults and children of various ages, including children of young age, wherein a possibility of free movement of the user during the correction process is ensured with preservation of a possibility of active movements in large joints of the lower extremities (hip, knee, and talocrural joints) and the simultaneous step-by-step elimination of various singular or combinatorial pathological configurations of segments of the lower extremities.

The proposed method for correcting pathological configurations of segments of the lower extremities is carried out as follows.

The proposed method is meant for the step-by-step elimination of various pathological configurations of segments of one or both lower extremities (thigh, tibia, foot), singularly or in combination. Said pathological configurations may include, for example, hip(s) adduction; inner rotation of the hip(s); inner rotation of the entire lower extremity (lower extremities); flexion of the tibia(s) or recurvation of the tibia(s); varus or valgus positioning of the tibia(s); equine positioning or dropping of the foot (feet); adduction or abduction of the foot (feet) and other pathological configurations that can be a consequence of various combinations of above-Listed configurations.

The proposed method for correcting pathological configurations of segments of the lower extremities comprises the correction of pathological configurations of segments of one or both lower extremities using an orthopedic device. This device comprises a biomechanical rotational-correcting apparatus for the lower extremities, which we term modular exoskeleton. The modular exoskeleton is executed with a possibility of adjustment for a given user, and with a possibility of re-tuning during its use. The modular exoskeleton comprises the first, second, and third modules, as well as other means executed so that they can be used autonomously or in a given combination depending on the type of pathological configurations of the user's lower extremities. The proposed device will be described in more detail below, along with a description of a specific version of the proposed exoskeleton.

Upon application of the proposed method as a means of said correction, one carries out the step-by-step correction of the position of the longitudinal axes of those segments of one or both lower extremities that have singular or combinatorial pathological configurations.

This correction is carried out in the horizontal and/or frontal and/or sagittal planes. Depending on the presence of pathological configurations in the user, correction can be carried out separately and in each plane, in various combinations of planes, or in all planes simultaneously.

Said correction is carried out by means of simultaneously carrying out the dosed elimination of the imbalance of forces in the muscles supporting the corresponding joints and reduction of the pathological configurations of said segments, and the subsequent fixation of these segments in the correct position at each step of the correction using said orthopedic device comprising at least one module of said modular exoskeleton, executed with a possibility of individual adjustment and bringing, at each step of the correction, the position of the longitudinal axis of each pathologically configured segment closer to the physiologically correct position. Moreover, fixation of said segments in the corrected position at each step is carried out with a possibility of movements in the corresponding joints around the corrected biomechanical rotation axes of the corresponding joints in the predetermined range defined by said modular exoskeleton. As a result, the user's movement stereotype in the corresponding joints is brought closer to the physiologically correct movement stereotype.

If the user has a pathological configuration of only one segment, only one module from the above-indicated modules is used and the corresponding correction is carried out in those planes that are needed at a given pathological configuration. If the user has pathological configurations in various combinations of segments, corresponding combinations of said modules or parts comprising them are used and the correction of pathological configurations of the corresponding segments is carried out in the required planes.

The position of said planes is determined, while applying the proposed method, when the user assumes the position "standing,"

Fixation of said segments in the corrected position at each step with the use of the corresponding modules is carried out when the user assumes the position "lying down."

Following fixation of the corresponding modules, the user's position is changed to "standing" and in this position the user is able to move and painlessly carry out any actions connected to movement in many joints, including the corrected ones.

The number of corrective steps is specific for each user and depends on the degree to which segments of the lower extremities are pathologically configured, the starting muscle tone of the user, user's tolerance to physical exertion, and the rate of his/her physiological growth.

It is preferable to use the proposed method in the mode of continuous application while awake during a prolonged period (for example, one year and longer).

In certain conditions that the user has, for example adductor syndrome, pathological configurations of segments are reduced in the step-by-step manner via adducting the hip in the corresponding hip joint. Moreover, the correction of said configurations is carried out by the simultaneous dosed extension of hip adductors and the dosed correction of the position of the femoral head in the socket of the corresponding hip joint by abducting the hip in the frontal plane and subsequent fixation of the corrected position using the first module of the exoskeleton, thus ensuring a possibility of movements in the corresponding hip joint in the horizontal, frontal, and sagittal planes within a predetermined range defined by said first module.

In the case of pathological prone (inner rotational) configuration of the hip, its dosed outer rotation in the horizontal plane is carried out simultaneously with the dosed hip abduction in the frontal plane.

At each step of said correction, the position of the femoral head in the socket of the corresponding hip joint is brought closer to the physiologically correct position wherein at each step, the dosed extension of hip adductors, the dosed hip abduction, and the dosed changing of the position of the femoral head in the hip socket of the corresponding hip joint are carried out in the range that avoids painful sensations for the user.

Moreover, the number of steps is chosen so that it allows, without the user's experiencing painful sensations, gradual achievement of the physiologically correct position of the longitudinal axis of the corresponding lower extremity when the user assumes the position "standing."

As necessary, pathological configurations of segments are reduced in the step-by-step manner by hips' adduction in the corresponding hip joints of both lower extremities, the correction of which is carried out independently for each hip joint without cross-effect. Moreover, depending on the degree of pathological configurations of the hips, a distinct degree is secured for the dosed extension of adductors in each hip, dosed abduction of each hip, and dosed change of the position of the femoral head in the hip socket of the corresponding hip joint.

In case of certain diseases, such as ICP, pathological configurations of segments such as inner rotation of the lower extremity (its hip and tibia) are reduced in the step-by-step manner. Moreover, the correction of said configurations is carried out by the simultaneous dosed elimination of the imbalance of forces in the muscles supporting the corresponding hip joints, and outer rotation of the lower extremity in the corresponding hip joint. Following which, fixation of the corrected position is carried out using the first and second modules of the exoskeleton, which enables a possibility of movements in the corresponding hip and knee joints in the predetermined range defined by said first and second modules.

At each step, dosed outer rotation of the corresponding hip and tibia in the corresponding hip joint and dosed elimination of the imbalance of forces in the muscles supporting the corresponding hip joint are carried out in the range that precludes the user's experiencing painful sensations.

If there are indications, the step-by-step reduction of pathological configurations of segments such as inner rotation of both lower extremities is carried out, and the correction is done independently for each lower extremity without cross-effect. Moreover, depending on the degree of pathological configurations, a distinct degree is secured for the dosed outer rotation of the corresponding lower extremity in the corresponding hip joint, and dosed elimination of the imbalance of forces in the muscles supporting the corresponding hip joint.

Moreover, a number of steps of said correction are selected that, without the user's experiencing painful sensations, gradually achieves the physiologically correct position of the longitudinal axis of the corresponding lower extremity when the user assumes the position "standing."

In case of certain conditions, for example lower atonic or spastic paraparesis, pathological configurations of segments such as recurvation of the tibia in the corresponding knee joint are reduced, wherein the correction of said configurations is carried out by the dosed limitation of tibia extension in the corresponding knee joint in the sagittal plane at the time of support during locomotion, and fixation of the corrected position using the second module of the exoskeleton that allows a possibility of flexion and extension of the tibia in the knee joint in the sagittal plane in the predetermined range defined by said second module.

If necessary, pathological configurations of segments such as recurvation of tibias in the corresponding knee joints of both lower extremities are reduced, and the correction is done independently for each knee joint without cross-effect. Moreover, depending on the degree of pathological configurations, a distinct degree of the dosed limitation of possible recurvation of each tibia is secured in the corresponding knee joint.

In case of certain diseases, such as ICP, pathological configurations such as tibia flexion in the knee joint are reduced in the step-by-step manner. Moreover, the correction of said configurations is carried out by the simultaneous dosed elimination of the imbalance of forces in the muscles supporting the knee joint and limitation of flexion of the tibia in the corresponding knee joint in the sagittal plane at the time of support during locomotion, and the subsequent fixation of the corrected position using the spring-assisted second module of the exoskeleton, allowing a possibility of flexing and extending the tibia in the knee joint in the predetermined range defined by said second module.

If necessary, pathological configurations of segments such as tibia flexion in the corresponding knee joint of both lower extremities are reduced in the step-by-step manner. Moreover, said correction is carried out using two spring-assisted second modules of the exoskeleton independently for each knee joint and without cross-effect. Further, depending on the degree of pathological configurations, distinct degrees of the dosed elimination of the imbalance of forces in the muscles supporting the knee joint and the dosed limitation of tibia flexion in the corresponding knee joint are secured.

Moreover, at each step of the correction, the dosed elimination of the imbalance of forces in the muscles supporting the corresponding knee joint and dosed limitation of tibia flexion in the corresponding knee joint are carried out in the range that precludes the user's experiencing painful sensations. Further, the selected number of steps allows, without the user's experiencing painful sensations, gradual achievement of the physiologically correct position of the longitudinal axis of the corresponding lower extremity when the user assumes the position "standing."

In case of certain diseases and conditions, such as ICP or complications of metabolic diseases, pathological configurations of segments such as varus and valgus positioning of the tibia in the knee joint are reduced in the step-by-step manner. Moreover, the correction of said configurations is carried out by the simultaneous dosed elimination of the imbalance of forces in the muscles supporting the knee joint, and the correction of the tibia's position in the frontal plane. Following which, fixation of the corrected position is carried out using the second module of the exoskeleton, which allows a possibility of flexion and extension of the tibia in the knee joint in the sagittal plane in the predetermined range defined by said second module.

If necessary, pathological configurations of segments such as varus and valgus positioning of the tibias in both lower extremities are reduced in the step-by-step manner; their correction is carried out independently for each knee joint and without cross-effect. Moreover, depending on the degree of pathological configurations, distinct degrees of the dosed elimination of the imbalance of forces in the muscles supporting the corresponding knee joint and dosed extension of the corresponding tibia are secured.

At each step of the correction, the dosed elimination of the imbalance of forces in the muscles supporting the corresponding knee joint and dosed correction of the tibia's position in the frontal plane are carried out in the range that avoids painful sensations for the user. Further, the selected number of steps of said correction allows, without the user's experiencing painful sensations, gradual achievement of the physiologically correct positioning of the longitudinal axis of the corresponding lower extremity when the user assumes the position "standing."

In cases of certain diseases, such as ICP, pathological configurations of segments such as foot adduction or abduction in the talocrural joint are reduced in the step-by-step manner. Moreover, the correction of said configurations is carried out by the simultaneous dosed elimination of the imbalance of forces in the muscles supporting the talocrural joint and the corresponding abduction or adduction of the foot in the horizontal plane. Following which, fixation of the corrected position of the foot is carried out using the third module of the exoskeleton, allowing a possibility of plantar flexion and dorsiflexion of the foot in the talocrural joint in the sagittal plane within a range predetermined by said third module.

If necessary, pathological configurations of segments such as foot adduction or abduction in the corresponding talocrural joint of both lower extremities are reduced in the step-by-step manner, which is carried out independently for each foot and without cross-effect. Moreover, depending on the degree of pathological configurations, distinct degrees of the dosed elimination of the imbalance of forces in the muscles supporting the corresponding talocrural joint and the dosed abduction of the corresponding foot are secured.

Moreover, at each step of the correction, the dosed elimination of the imbalance of forces in the muscles supporting the corresponding talocrural joint and the dosed abduction and adduction of the corresponding foot are carried out in the range that avoids painful sensations for the user. Further, the selected number of steps allows, without the user's experiencing painful sensations, gradual achievement of the physiologically correct position of the longitudinal axis of the corresponding lower extremity when the user assumes the position "standing."

In cases of certain diseases, such as metabolic diseases or connective tissue dysplasia syndrome, pathological configurations of segments such as varus and valgus positioning of the foot in the talocrural joint are reduced in the step-by-step manner. Moreover, the correction of said configurations is carried out by the simultaneous dosed elimination of the imbalance of forces in the muscles of the calf and changing the position of the foot in the talocrural joint in the frontal plane up to the alignment of the longitudinal axis of, at least, the heel bone of the foot with the physiologically correct position of the longitudinal axis of the corresponding lower extremity. Following which, fixation of the corrected position of the foot is carried out using the third module of the exoskeleton and individual correcting inserts that are positioned onto the inner or outer surface of the means for accommodating the foot of the exoskeleton, allowing the possibility of plantar flexion and dorsiflexion of the foot in the talocrural joint in the sagittal plane within a range predetermined by said third module.

If necessary, pathological configurations of segments such as varus and valgus positioning of the foot in both lower extremities are reduced in the step-by-step manner, and their correction is carried out independently for each foot. Moreover, depending on the degree of pathological configurations, a distinct degree of changing the position of the foot in the corresponding talocrural joint is secured.

Moreover, at each step of correction, the dosed change of the position of the foot in the talocrural joint is carried out in the range that avoids painful sensations for the user. Further, the selected number of steps allows, without the user's experiencing painful sensations, gradual achievement of the physiologically correct position of the longitudinal axis of the corresponding lower extremity when the user assumes the position "standing."

In cases of certain diseases, such as ICP or neuropathy of the fibular nerve, pathological configurations of segments such as equine positioning of the foot or dropping of the foot in the talocrural joint are reduced in the step-by-step manner. Moreover, the correction of said configurations is carried out by the simultaneous dosed extension of the triceps muscle of the corresponding calf and limiting plantar flexion of the foot in the sagittal plane. Following which, fixation of the corrected position is carried out using the third module of the exoskeleton, allowing a possibility of dorsiflexion of the foot in the talocrural joint in the sagittal plane in the predetermined range defined by said third module.

If necessary, pathological configurations of segments such as equine positioning of the foot or dropping of the foot in the corresponding talocrural joint of both lower extremities are reduced in the step-by-step manner, which is carried out independently for each foot and without cross-effect. Moreover, depending on the degree of pathological configurations, distinct degrees of the dosed extension of the triceps muscle of the corresponding calf and limiting plantar flexion of the foot are secured.

At each step of correction, the dosed extension of the triceps muscle of the corresponding calf and limiting dorsiflexion of the foot are carried out in the range that avoids painful sensations for the user. Further, the selected number of steps allows, without the user's experiencing painful sensations, gradual achievement of the physiologically correct position of the longitudinal axis of the corresponding lower extremity when the user assumes the position "standing."

Between the steps of the corresponding correction, various active exercises of dynamic nature can be performed, until there is a decrease in the tone of the corresponding muscles. Moreover, it is possible to apply various influences on the user, for example manual, device-mediated, physical therapy, and medicinal options. Wherein said influences can be used alone or in combination.

As medicinal influence options, one can use, for example, the following medications: preparations of botulinum toxin type "A," muscle relaxants, and local anesthetics. As physical therapy options, one can use, for example, electric stimulation of the muscles including functional electric stimulation of muscles during walking (artificial correction of movements), oscillatory therapy, cryotherapy, and cryocontrast.

All of the aforesaid leads to, upon application of the proposed method, the step-by-step continuous correction of the position of longitudinal axes of the lower extremities (one or both) via elimination of singular or combinatorial pathological configurations of the hip, tibia, and/or foot. Step-by-step, pain-free changes in the position of biomechanical rotation axes and passive limitations or restoration of the range of movement in the large joints of the lower extremities (hip, knee, and talocrural) are achieved. For this, the step-by-step adjustment of the structural elements of the modular exoskeleton is carried out so as to achieve the maximal approximation of the movement stereotype of the user to the physiologically correct movement stereotype while avoiding painful sensations for the user.

Moreover, use of the proposed method ensures achievement of the physiologically correct position of longitudinal axes of segments of the left and/or right lower extremity with preservation of the possibility of active movements in the large joints, which is a prerequisite for developing active locomotive skills in the process of continuous correction and precludes the negative influence of a prolonged immobilization on the musculoskeletal and central nervous system of the user.

BRIEF DESCRIPTION OF THE DRAWINGS

To better understand the present invention, below there is a detailed description of its specific execution that is not sole and/or exclusive within the execution framework of the method being patented and the device for correcting pathological configurations of segments of the lower extremities, with references to the enclosed drawings, in which.

THE PREFERRED EMBODIMENT OF THE INVENTION

Figure 1:
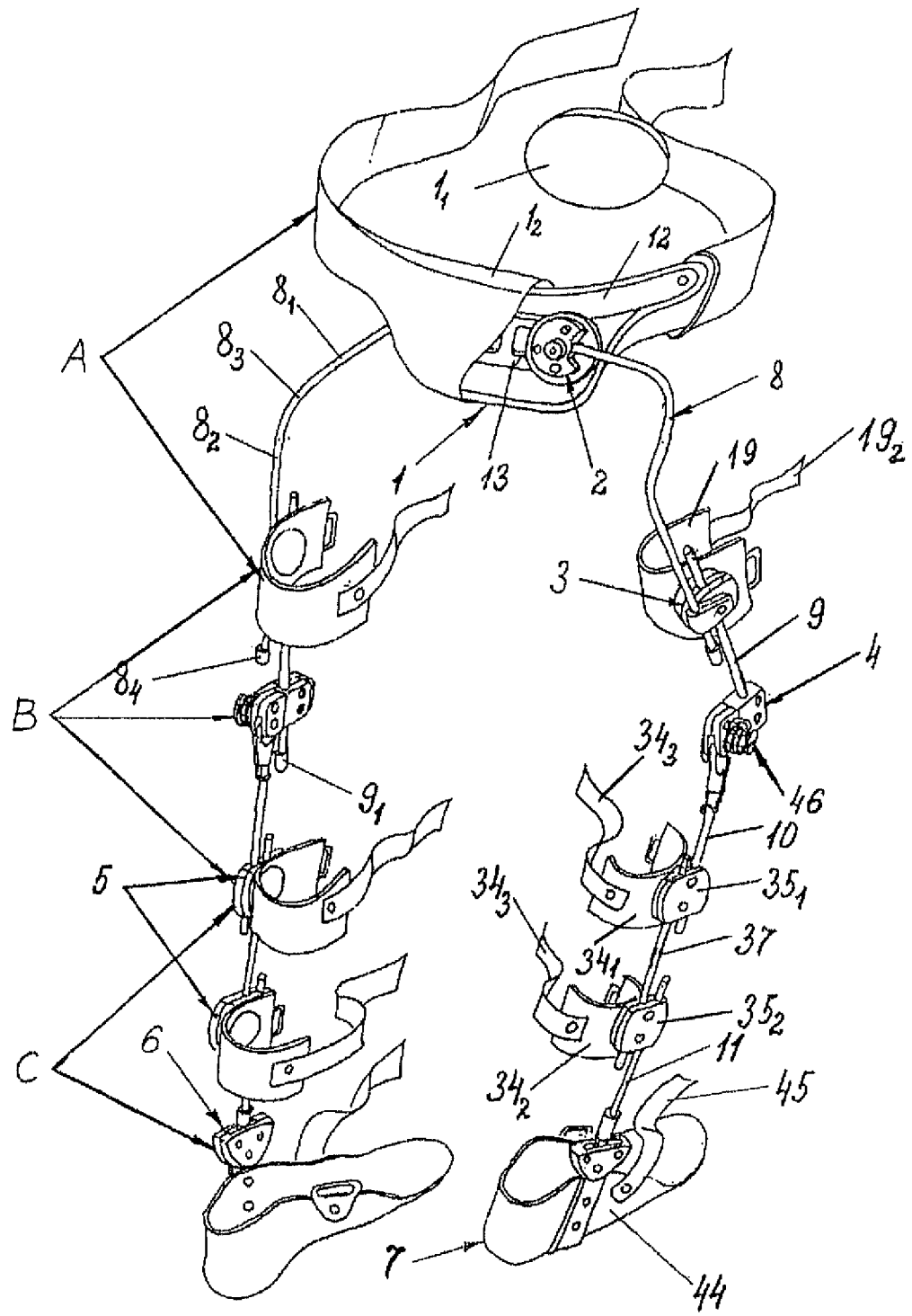
FIG. 1 depicts a schematic of the device for correcting pathological configurations of segments of the lower extremities, general view, according to the invention.

The proposed device for correcting pathological configurations of segments of the lower extremities comprises a biomechanical rotational-correcting apparatus for the lower extremities, termed modular exoskeleton. The exoskeleton contains adjustable pelvic belt 1 (FIG. 1) positioned around the user's waist and executed with a possibility of centering the femoral head of at least one thigh in the hip socket of the hip joint. The possibility of centering the femoral head in the hip socket is enabled by at least one means 2 for centering the femoral head, executed with a possibility of holding the thigh in a given position and fastened on pelvic belt 1.

The exoskeleton also contains at least one means 3 for holding the thigh in a given position, at least one means 4 for rotating the tibia executed with a possibility of correcting the position of its rotation in the frontal and horizontal planes, at least one means 5 for holding the tibia in a given position executed with a possibility of turning the foot in the horizontal plane, at least one means 6 for correcting the position of the foot and the movement range thereof in the talocrural joint, and at least one means 7 for accommodating the foot.

In the version of the exoskeleton's execution presented in FIG. 1, all above-named means 2-7 are placed on both lower extremities of the user. However, said means 2-7 can be placed, if medically indicated, on one or both lower extremities of the user in various combinations.

To connect above-named means 2-6 with one another, the exoskeleton contains a set of connecting elements. Each connecting element comprises connecting cylindrical rods 8, 9, 10, 11 executed with a possibility of linear positioning movement and/or rotation and/or free linear movement.

The envisaged possibilities of linear movement (free or positional) and rotation of each rod 8, 9, 10, 11 will be reflected in more detail in the corresponding section pertaining to the detailed description of each above-named means 2-6. A common feature of rods 8, 9, 10, 11 is that each of them is executed in the form of a cylindrical rod, which allows a possibility of rotation, and free or positional linear movement. At the very least, the ends of a part of rods 8, 9, 10, 11 feature protective caps made of plastic, for example protective cap $9_1$ placed on the end of rod 9.

The exoskeleton being patented allows, if necessary, a possibility to carry out the correction of pathological configurations of all segments of the lower extremities and, in this case, contains all above-listed means 2-6 positioned on each lower extremity and connected with one another via the corresponding rods 8, 9, 10, 11.

Figure 2:
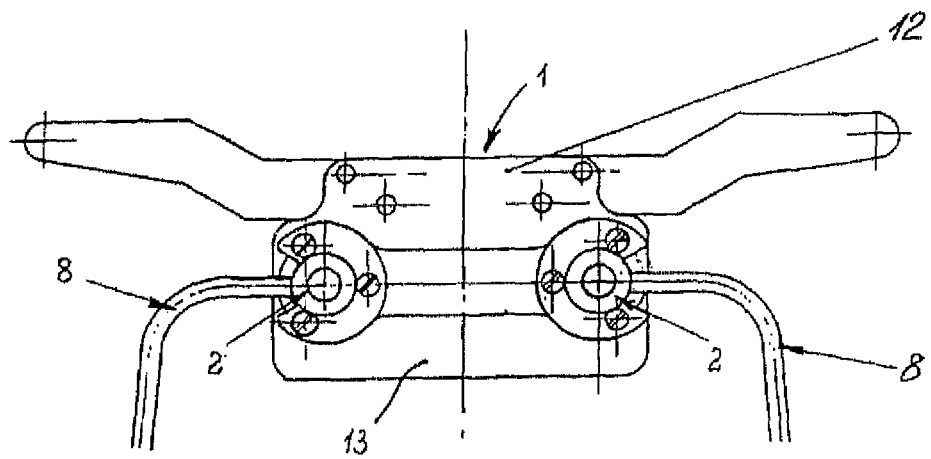
FIG. 2—the adjustable pelvic belt, according to the invention.

Adjustable pelvic belt 1 contains support plate 12 (FIGS. 1, 2) on which base 13 is fastened that is oriented along pelvic belt 1 and has a complex structure accounting for anatomical characteristics of the user. Base 13 comprises a plate stretched out horizontally with rounded corners, in the upper part of which there is a symmetrical narrowing. Corresponding means 2 for centering the femoral head is mounted on each of the opposing sides of base 13 of adjustable pelvic belt 1.

For the convenience of the user, pelvic belt 1 has a stop $1_1$ for positioning on the front wall of the abdomen. Stop $1_1$ is made of elastic material and has a removable closed cover $1_2$, in which corresponding means 2 for centering the femoral head is placed. In FIG. 1 closed cover $1_2$ is depicted as partially removed from pelvic belt 1.

Base 13 is dumbbell shaped and made of light metal selected from a group: titanium, titanium alloys, aluminum alloys, magnesium alloys; support plate 12 is made of durable plastic, for example polypropylene.

Each first rod 8 is made in the shape of a cylindrical pivot with a complex three-dimensional shape and has two straight-line segments $8_1$ and $8_2$, the first of which is oriented along the rotation axis of rod 8, and the second straight-line segment is essentially oriented along the user's tibia, and the third curvilinear segment $8_3$ smoothly connects first and second straight-line segments $8_1$ and $8_2$.

The length of straight-line segments $8_1$ and $8_2$ of first rod 8 corresponds to anthropomorphic parameters of the user and has at least three standard sizes defining the total length of first rod 8.

Each means for centering the femoral head 2 (FIGS. 3, 4) comprises flange 14 featuring a semi-spherical concavity, removable lid 15 firmly connected to flange 14 using, for example, a bolted connection, and featuring an inverse semi-spherical concavity, and sphere shaped hinge 16 firmly secured in said concavities with a possibility of free positional rotation to create a certain position of first rod 8 in the horizontal and frontal planes.

The first end of first rod 8 is fastened in sphere shaped hinge 16 with a possibility of free rotation. To enable free rotation of first rod 8, a through axial opening is made in hinge 16 in which gapped first end of first rod 8 is positioned that is fastened using any known method, for example using a nut flared in the opening or nut fastened using a screw connection or another known method.

To ensure positioning free movement of sphere shaped hinge 16, conical rabbeting is made in each flange 14 of base 13 and in each removable lid 15 at the location of each corresponding rod 8. Flat angle—at the apex of the conical rabbeting has a degree from 20° to 60° which ensures a wide range of positioning configurations of hinge 16. Said angle is selected with consideration of the specific pathology of a given user.

Figure 3:
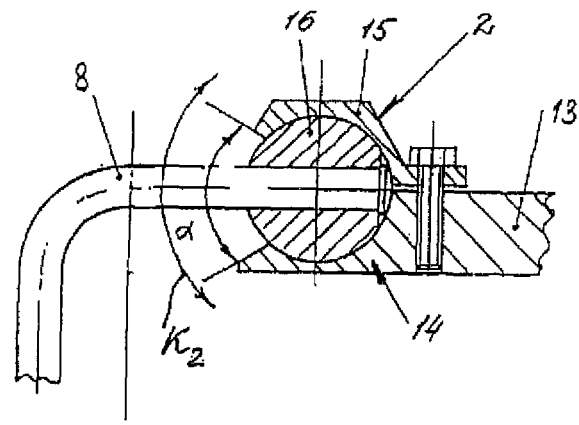
FIG. 3—the means for centering the femoral head, transverse section, according to the invention.
Figure 4:
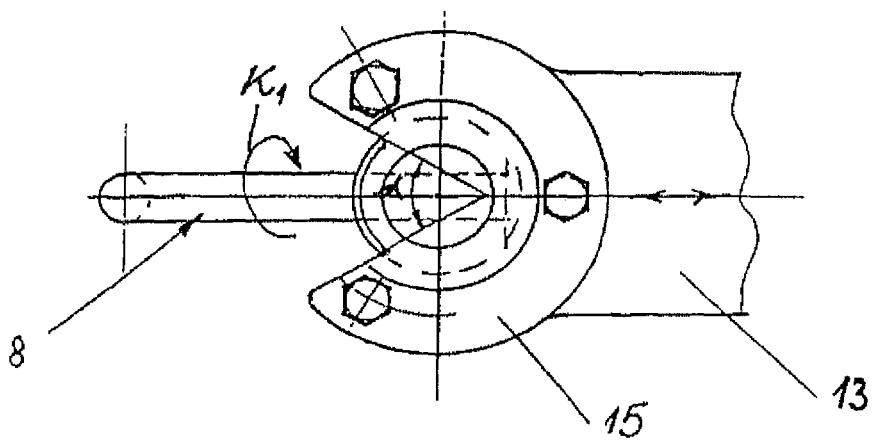
FIG. 4—same as FIG. 3, plan view, according to the invention.

In FIG. 4, arrow $K_1$ indicates a possibility of positioning rotations of hinge 16 in the frontal plane; in FIG. 3, arrow $K_2$ indicates a possibility of positioning rotations of hinge 16 in the horizontal plane, and a possibility of rotation of first rod 8 relative to hinge 16 while using the apparatus.

Figure 5:
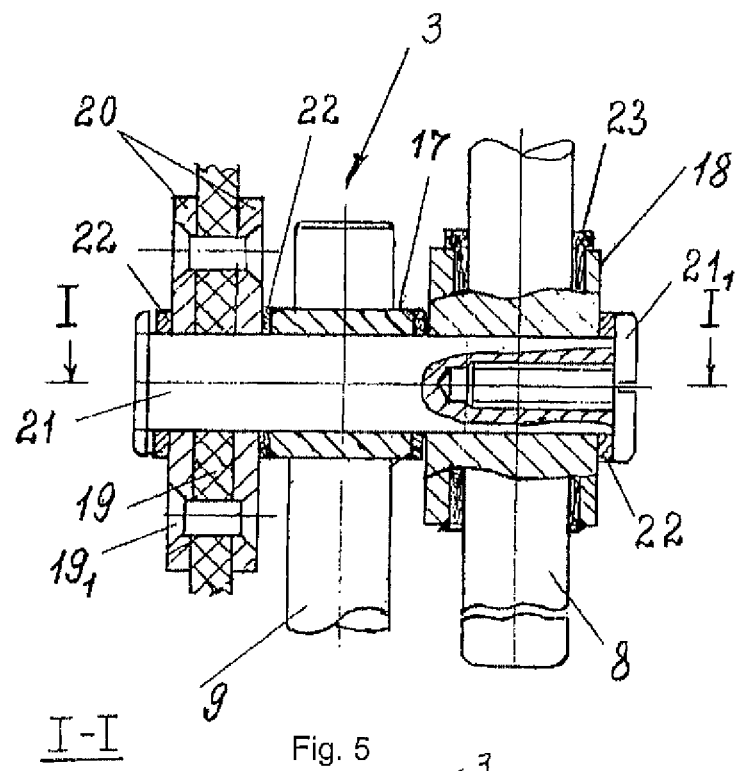
FIG. 5—the means for holding the thigh in a given position, longitudinal section, according to the invention.
Figure 6:
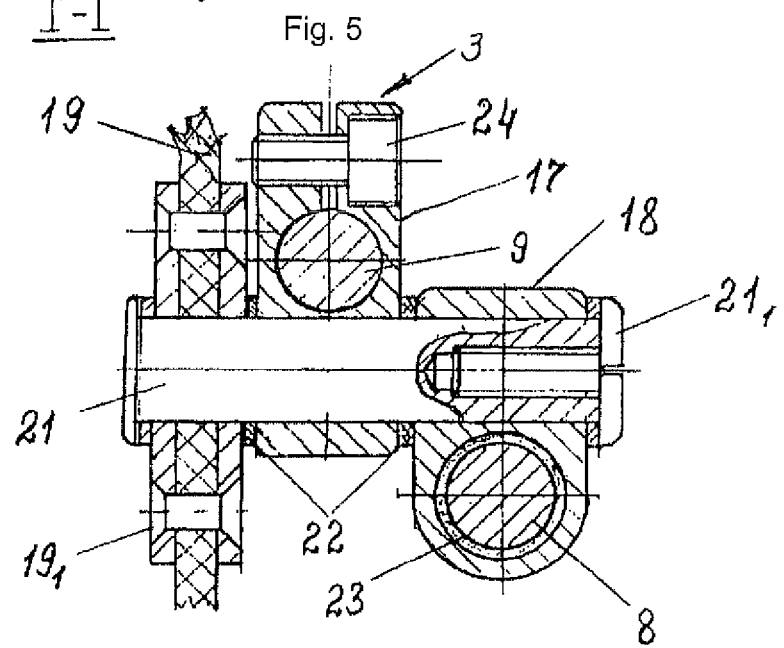
FIG. 6—section along line I-I in FIG. 5.

Means 3 for holding the thigh in a given position is made of two parts 17 and 18 (FIGS. 5, 6) situated with a possibility of free rotation of one relative to the other in the sagittal plane and with a possibility of positioning rotation in the horizontal plane.

The device contains an adjustable thigh cuff 19 on which, with a possibility of turning in the sagittal plane, the first part 17 of means 3 for holding the thigh in a given position is fastened having the first through channel in which, with a possibility of rotation and linear positioning movement, the first end of second rod 9 is secured, and the second through channel is made in second part 18 in which, with a possibility of linear free movement, the second end of first rod 8 is secured.

To ensure firmness of adjustable thigh cuff 19, metallic nuts 20 are provided, firmly locked from the opposite sides of cuff 19 using rivets $19_1$.

Moreover, means 3 for holding the thigh in a given position contains axle 21 connecting adjustable thigh cuff 19 with first and second parts 17, 18 of means 3 for holding the thigh. The ends of axle 21 are fastened with a possibility of free rotation on adjustable thigh cuff 19 and on second part 18 of means 3 for holding the thigh in a given position, for example using bolt $21_1$ fastened on axle 21. To avoid catching of rotating parts 17, 18 with each other, thigh cuff 19, and bolt $21_1$, nuts 22 made of, for example, fluorine plastic, are placed between the corresponding parts 17, 18, cuff 19, and bolt $21_1$.

To achieve a more smooth linear movement of first rod 8 along the second through channel, insert 23 is placed therein that is made of polymer material, for example polypropylene or fluorine plastic.

To facilitate placement of second rod 9 in first part 17 of means 3 for holding the thigh in a given position, this part 17 is executed as an assembled unit. Following placement of second rod 9, first part 17 is fastened using, for example, bolts 24.

Figures 7, 8, 9:
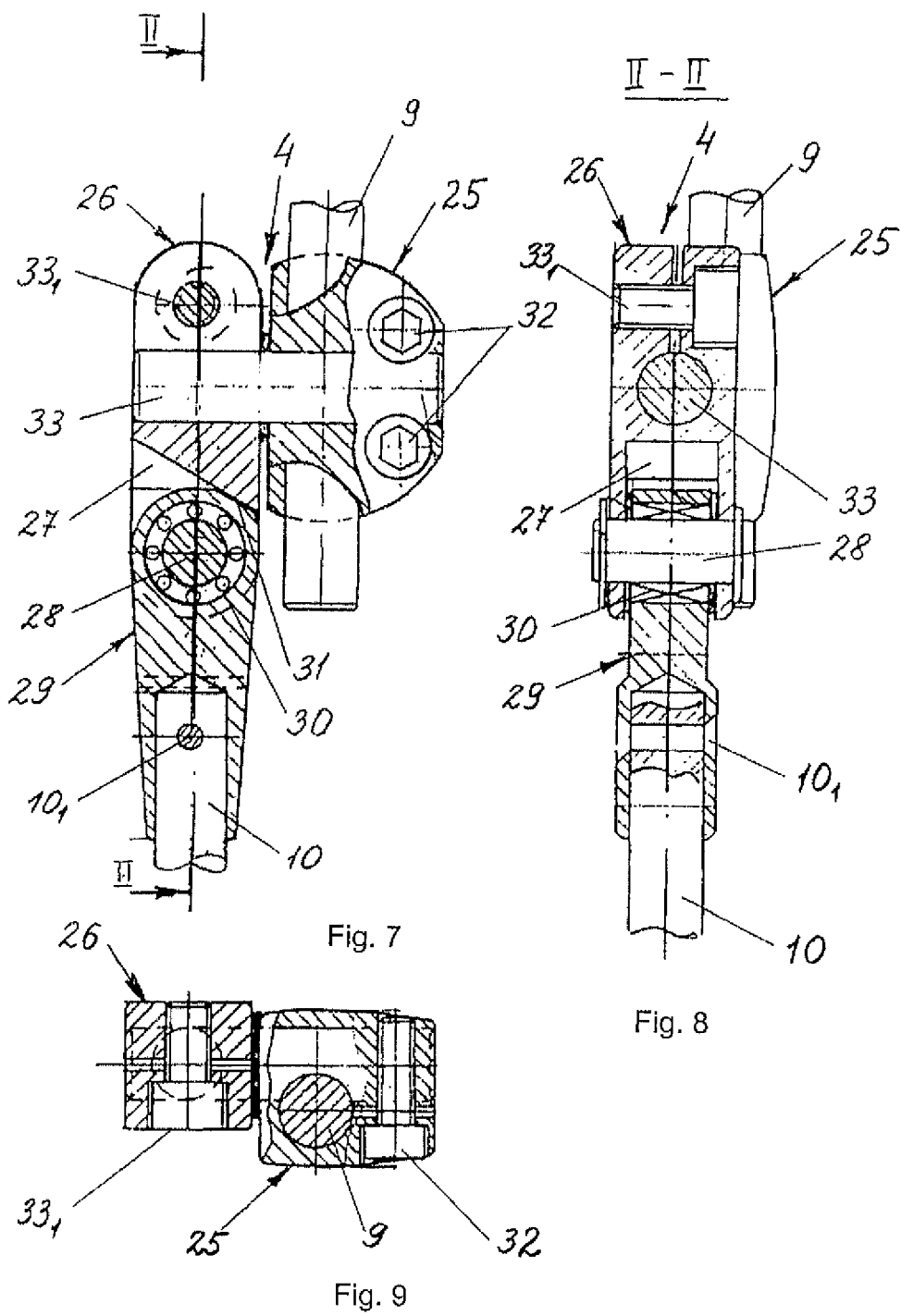
FIG. 7—the means for rotating the tibia, longitudinal section, according to the invention.
FIG. 8—section along line II-II in FIG. 7.
FIG. 9—view from above in FIG. 7 with sections and cutaways, according to the invention.

In the device being patented, means 4 for rotating the tibia is made of two parts 25, 26 (FIGS. 7, 8, 9) mounted with a possibility of positioning turning of one relative to the other in the frontal and horizontal planes. In first part 25, the third through channel is made in which, with a possibility of positioning linear movement, the second end of second rod 9 is secured, and in second part 26 of means 4 for rotating the tibia slit 27 is made in which, on axle 28, knee hinge 29 is placed that is executed with a possibility of limited flexion and extension of the tibia in the sagittal plane. To secure the first end of third rod 10 a socket is made in knee hinge 29 in which said end of third rod 10 is firmly fastened using, for example, rivet $10_1$.

There is a bearing for rotation of knee hinge 29 relative to axle 28, for example needle bearing 30, the axle of which serves as axle 28 of knee hinge 29.

At the site of slit 27 of second part 26 of means 4 for rotating the tibia, there is stop 31 (FIG. 7) limiting the turn of knee hinge 29 in the sagittal plane.

For convenient placement of second rod 9 in first part 25 of means 4 for rotating the tibia, this part 25 is executed as an assembled unit, and fastening is achieved using two bolts 32 firmly securing second end of second rod 9. In first part 25 of means 4 for rotating the tibia, there is a cylindrical protrusion serving as axle 33, relative to which positioning rotation of second part 26 of means 4 for rotating the tibia is carried out in the frontal and horizontal planes. Fixation of axle 33 is carried out, following its placement in a defined position, using bolt $33_1$.

Described means 4 for rotating the tibia allows correction of the position of the tibia in the horizontal and frontal planes and simultaneously carries out the defined flexion-extension of the tibia in the sagittal plane during locomotion (movement).

Presence of stop 31 limits recurvation of the tibia during the period of support upon locomotion.

Figure 10:
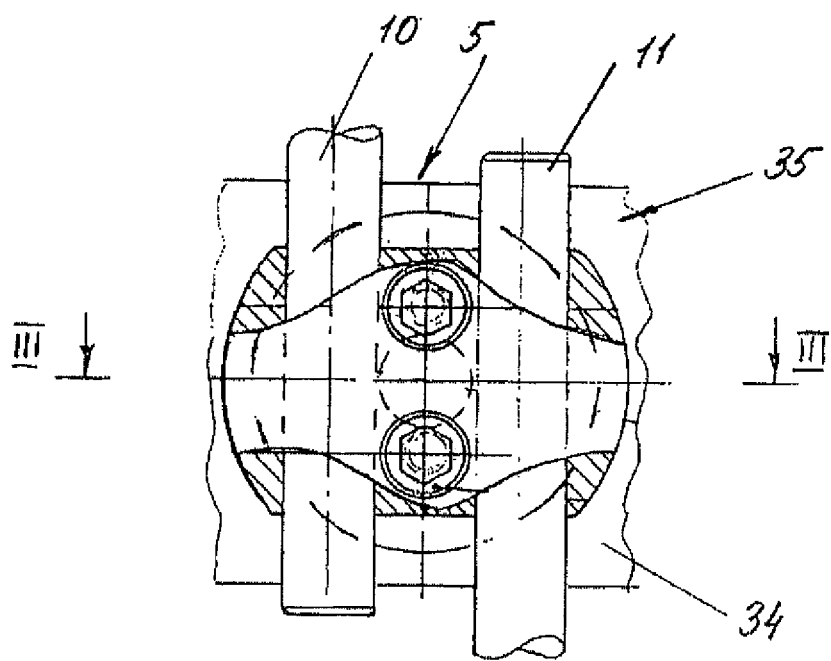
FIG. 10—the means for holding the tibia in a given position, longitudinal section with cutaways, according to the invention.
Figure 11:
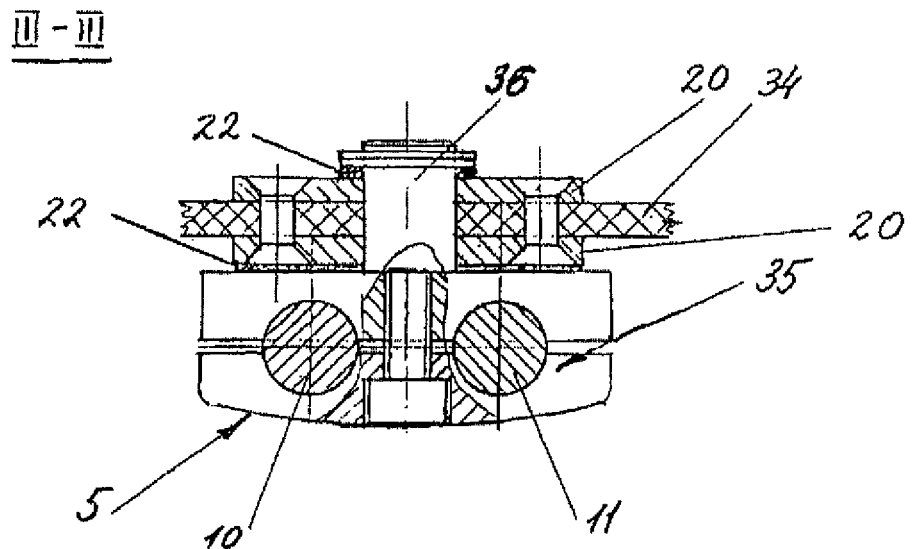
FIG. 11—section along line III-III in FIG. 10, with cutaways.

In the described version of the device, means 5 for holding the tibia in a given position contains adjustable calf cuff 34 (FIGS. 10, 11) and base 35, having the fourth and the fifth through channels in which, with a possibility of linear positioning movement, the second end of third rod 10 and the first end of fourth rod 11 are secured, respectively. Base 35 has axle 36 on which, with a possibility of rotation in the sagittal plane, adjustable calf cuff 34 is secured.

For convenient placement of third and fourth rods 10, 11 in base 35, this base 35 is executed as an assembled unit, and fastening of parts of base 35 is done using bolt connection.

In cases when the length of the user's tibia is not great and its volume does not change substantially along its length, it is sufficient to use means 5 for holding the tibia in a given position having one base 35 fastened on one calf cuff 34 that is usually positioned in mid-calf. Moreover, cuff 34 is securely fastened on the calf, which does not cause inconvenience when the apparatus is in use. Analogous to how it is executed in thigh cuff 19, metallic nuts 20 are placed from both sides of cuff 34 that confer the necessary firmness that prevents twisting of calf cuff 34. To avoid catching, during rotation, between adjoining elements (i.e. between nut 20 and axle 36, and between nut 20 and base 35), nuts 22 are placed between them that are made of, for example, fluorine plastic.

In cases when the user's calf's volume changes substantially along the length, it is difficult to ensure, using one calf cuff 34, tight fit of third and fourth rods 10, 11 to the tibia and reliable fastening of cuff 34. In such a case, means 5 for holding the tibia in a given position contains two analogously executed calf cuffs $34_1$ and $34_2$ (see FIG. 1), each of which is mounted on corresponding base $35_1$ and $35_2$. To connect bases $35_1$ and $35_2$, the apparatus has intermediate rod 37 (FIG. 1). In each base $35_1$ and $35_2$, sixth and seventh through channels are made whereby in the sixth through channel of first base $35_1$ the second end of third rod 10 is firmly secured and in the seventh through channel of first base $35_1$, with a possibility of linear positioning movement, the first end of intermediate rod 37 is secured. In the sixth and the seventh through channels of second base $35_2$, with a possibility of linear positioning movement, the second end of intermediate rod 37 and the first end of fourth rod 11 are secured, respectively. Moreover, each base $35_1$ and $35_2$ has axle 36 (FIG. 11) on which, with a possibility of rotation in the sagittal plane, corresponding adjustable calf cuff $34_1$, $34_2$ is secured (FIG. 1).

All above-mentioned cuffs—adjustable thigh cuff 19 and adjustable calf cuffs 34, $34_1$, $34_2$—are made of durable plastic, for example foam polyethylene, polyurethane, ultrathene or other like materials, and feature fastenings $19_2$ and $34_3$, respectively, for example Velcro-like.

In FIG. 1, a version of the device being patented is depicted in which means 5 for holding the tibia in a given position is executed with two cuffs $34_1$, $34_2$ positioned on the user's calf as described above.

To achieve a better fit to the tibia, intermediate rod 37 can be executed as straight-line as shown in FIG. 1, or curvilinear along the shape of the user's tibia.

The version of the apparatus with two calf cuffs $34_1$, $34_2$, one of which is positioned in the upper part under the knee and the other—in the lower part, affords a more reliable performance of means 5 for holding the tibia in a given position and precludes tilts and poor fit.

Figure 12:
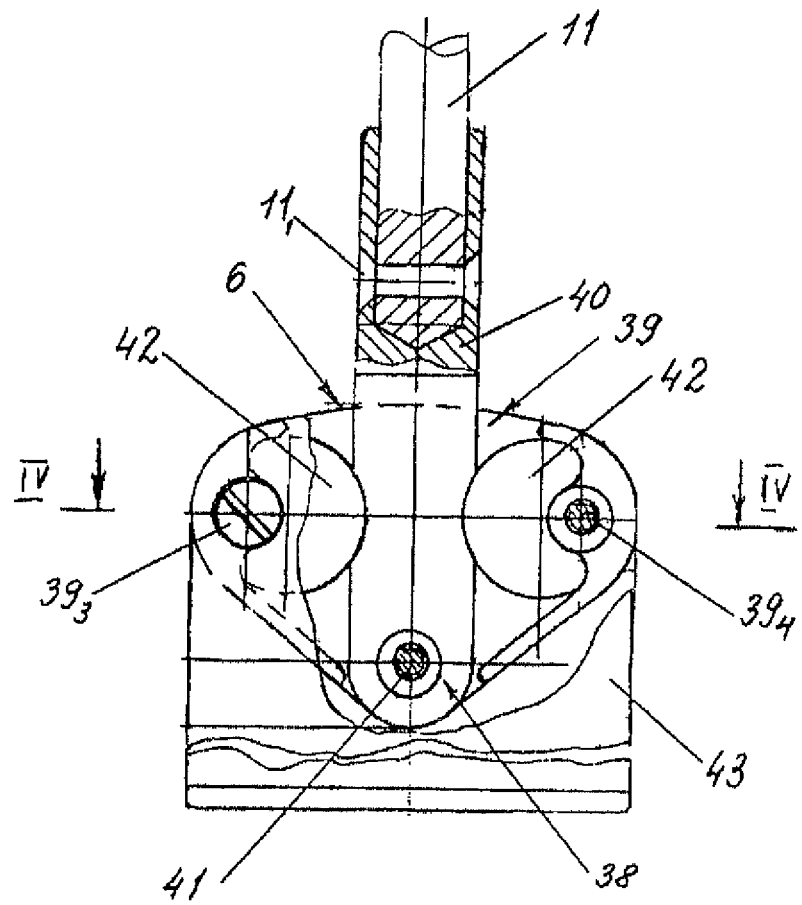
FIG. 12—the means for holding the foot relative to the talocrural joint and correcting the movement range thereof, longitudinal section, with cutaways, according to the invention.
Figure 13:
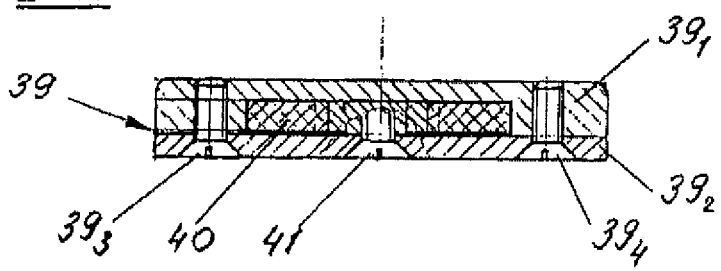
FIG. 13—section along line IV-IV in FIG. 12.

In the described version of the proposed device, means 6 for the correction of the position of the foot and the movement range thereof in the talocrural joint contains talocrural hinge 38 (FIGS. 12, 13) having hollow body 39, in which tip 40 is fastened. On one end of tip 40, the second end of fourth rod 11 is firmly secured using, for example, using rivet $11_1$, and the other end of tip 40 is secured in hollow body 39 on axle 41 of talocrural hinge 38 with a possibility of rotation in the sagittal plane. Body 39 comprises two parts $39_1$, $39_2$ connected with each other using bolts $39_3$, $39_4$.

To achieve smooth movement of talocrural hinge 38 in hollow body 39 of means 6 for correcting the position of the foot and the movement range thereof in the talocrural joint, at least one spring element 42 is installed (in the described version, there are two spring elements 42) in hollow body 39, executed with a possibility of limiting the turn of the foot in the sagittal plane. One or two spring elements 42 create more favorable conditions for utilization of the proposed device and are made of, for example, latex or rubber.

The device contains connecting plate 43 with its one end fastened to axle of talocrural hinge 38 (FIG. 12) with a possibility of turning in the sagittal plane, and the other end firmly fastened to means 7 (FIG. 1) for accommodating the foot, which contains boot 44 and fastening elements 45 for holding the foot. Boot 44 of means 7 for accommodating the foot corresponds to the length of the user's foot and can be made with or without a nose part. If necessary, boot 44 of one size can be exchanged for boot 44 of another size.

Figure 14:
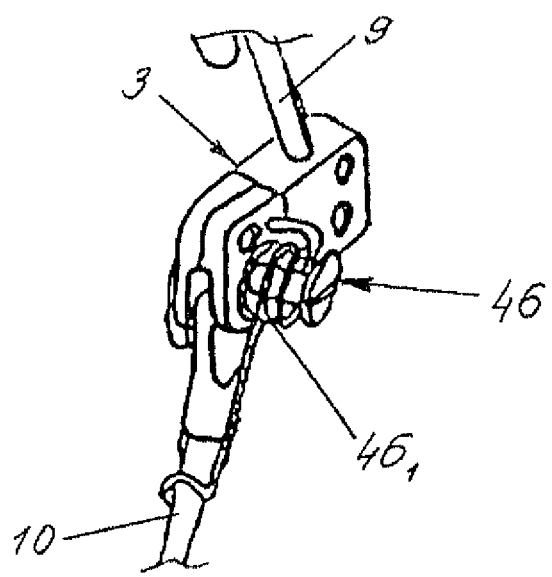
FIG. 14—the means for extending the knee joint, according to the invention.

If it is medically necessary to facilitate extension of the knee joint, the apparatus may contain means 46 (FIGS. 1, 14) for extending the knee joint secured in the zone in which the corresponding ends of second and third rods 9, 10 are located.

In the described version of execution of present invention, means 46 for extending the knee joint contains at least one spring $46_1$ (FIG. 14), one end of which is fastened on second part of means 4 (FIG. 1) for turning the tibia, and its other end—on the first end of third rod 10.

In other versions of execution of the apparatus being patented, means 46 for extending the knee joint may contain at least one mover (not shown in the drawing) placed in the zone in which the corresponding ends of second and third rods 9, 10 are located.

If it is medically necessary to facilitate movement of the thigh, the apparatus may contain a mover (not shown in the drawing) fastened on adjustable pelvic belt 1 of the thigh in the zone in which means 2 for centering the femoral head is located.

The apparatus being patented is characterized in that it is possible to carry out correction of pathological configurations of various segments of the lower extremities.

Let us examine in more detail the practicability of using said means 2-6 depending on several specific pathologies of segments of the lower extremities.

If the user has a pathological configuration of the thigh, when there is an inner rotation of the thigh or thigh adduction, the apparatus contains an adjustable pelvic belt executed with a possibility of centering the femoral head in the hip socket, and at least one means 3 for holding the thigh in a given position, connected by first rod 8 that is executed with a possibility of rotation and free linear movement.

Said construction units comprise first module A, executed with a possibility of positioning rotation in the horizontal plane and rotation of the thigh under static conditions and during movement (locomotion).

If the user has varus or valgus configuration of the tibia, the apparatus contains at least one means 3 for holding the thigh in a given position, at least one means 4 for rotating the tibia, and at least one means 5 for holding the tibia in a given position that are connected using second and third rods 9, 10, respectively. Moreover, second rod 9 is executed with a possibility of rotation and linear positioning movement, and third rod 10 is executed with a possibility of linear positioning movement.

Said means 3, 4, 5 comprise second module B, executed with a possibility of changing the position of the thigh in the horizontal and frontal planes.

To achieve a better effect from using the apparatus in cases of varus or valgus configurations of the tibia or the foot, it is preferable to use module A together with module B.

If the user's foot is in equine position or there is foot adduction or abduction, the apparatus contains at least one means 5 for holding the foot in a given position and at least one means 6 for correcting the position of the foot and the movement range thereof in the talocrural joint, connected using fourth rod 11 that is executed with a possibility of linear positioning movement.

Said means 5, 6 comprise third module C, executed with a possibility of outer and inner rotation of the tibia and the foot in the horizontal plane.

If the user's foot is in equine position or there is foot adduction or abduction, better results can be obtained by using second module B together with third module C.

As noted above, said first, second, and third modules A, B, and C are executed with a possibility of autonomous use or in a given combination, depending on the type of pathological configurations of the user's lower extremities.

Before using the apparatus in its entirety or separate modules thereof, an apparatus of the required size is selected for the user. Mainly apparatuses of three sizes are used, whereby there is a possibility of regulating separate modules lengthwise by changing the length of separate rods 8-11, 37. Moreover, there is a possibility of creating a custom apparatus manufactured for a given user.

Let us examine the process of putting the proposed modular exoskeleton on the user, having first, second, and third modules A, B, C and all means 2, 3, 4, 5, 6, 7 positioned on both lower extremities of the user.

First, calf cuffs $34_1$, $34_2$ and boot 44 are put on and their position fixed using fastenings $34_3$ and fastening elements 45, and the lengths of rods 10, 11, 37 are selected. Moreover, the lengths of rods 10, 11, 37 are selected in such a way as to have axle 28 of knee hinge 29 projected a bit higher (approximately by 2 cm) relative to the cavity of the knee joint.

Subsequently, adjustable pelvic belt 1 (FIG. 1) is put on the user's pelvic area, securing its tight fit with the user's body. Then, the user's thighs are placed into thigh cuffs 19 that are secured in the lower third of the thigh using fastenings $19_2$ so that cuffs 19 do not end up under knee joints, after which the length of rod 9 is set.

After the user puts on the apparatus and the lengths of rods 9, 10, 11, 37 are set, means 2 for centering the femoral head, means 4 for rotating the tibia, and means 6 for correcting the position of the foot and the movement range thereof in the talocrural joint are set out in such a position of the corresponding means 2, 4, 6 as to achieve correction of the position of the rotation axes of the hip, knee, and talocrural joints in the horizontal and frontal planes.

For correcting the position of the rotation axis of the hip joint, sphere shaped hinges 16 (FIGS. 3, 4) are situated in mid-position at which the axis of first rod 8 is parallel to the longitudinal axis of base 13.

In this position, hips' abduction in the positions "sitting" and "standing" proceeds essentially with the same abduction angles.

By turning sphere shaped hinge 16 with first rod 8 in the horizontal plane, various angles of abduction in the position "sitting" and the position "standing" are secured.

Using approximation methodology, the optimal direction of the axis of the corresponding first rod 8 is selected, and the position of the corresponding sphere shaped hinge 16 is fixed by bolt connection. Such a position of sphere shaped hinge 16 and first rod 8 connected thereto corresponds to the prescribed correction of the thigh and does not cause the user to experience painful sensations.

If necessary, the proposed modular exoskeleton can be custom adjusted for each hip joint of a given user without cross-effect, which favorably distinguishes it from known constructions of analogous utility.

To correct the position of the rotation axis of the knee joint in the horizontal plane, tightening of two bolts 32 (FIG. 7) of first part 25 of means 4 for rotating the tibia that hold the position on the second end of second rod 9 is loosened, and means 4 for rotating the tibia is turned in the horizontal plane together with the user's lower extremity. Subsequently, the lower extremity is held in the selected position and bolts 32 are tightened.

To correct the position of the rotation axis of the knee joint in the frontal plane, tightening of bolt $33_1$ of second part 26 of means 4 for rotating the tibia that holds the position of second part 26 on axle 33 is loosened, third rod 10 is dislodged and held in a selected position together with the user's tibia, and the position of the tibia is fixed by tightening bolt $33_1$.

To correct the position of the rotation axis of the talocrural joint in the horizontal plane, tightening of two bolts $35_1$, $35_2$ (FIGS. 10, 11) on base 35 is loosened, the user's foot is turned together with boot 44 in the desired direction by rotating the first end of fourth rod 11 in the fifth through channel of base 35, and the foot is held and fixed in the corrected position by tightening bolts $35_1$, $35_2$ of base 35.

Because the exoskeleton being patented features a simple construction, it can be used together with other devices that allow solving of the problem of correcting pathological configurations of the lower extremities, especially in children. For example, the proposed modular exoskeleton can be used together with a device for treating diseases of the locomotive system known from patent RF No. 2241500, apparatus "Gravistat"® or other similar devices allowing correction, along with that of pathological configurations of segments of the lower extremities, of pathological configurations of segments of the upper extremities and/or the body of the user, separately or in combination. This favorably distinguishes the proposed method and device from those already known.

Below, we examine yet another version of executing the proposed device for correcting pathological configurations of segments of the lower extremities which, in its construction, partially differs from the above-described version and features a more simple construction, which will be described below.

Said version of execution of the present invention will be discussed as applicable to correcting pathological configurations of segments of both lower extremities.

Figure 15:
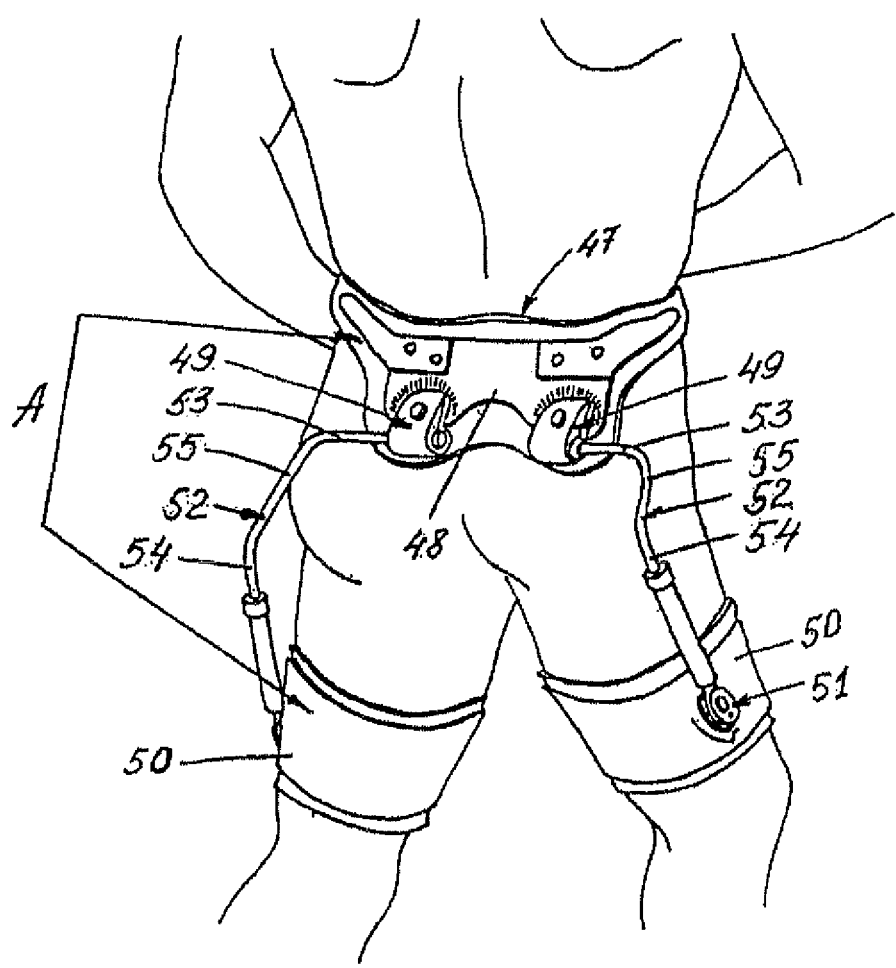
FIG. 15—a version of executing the device for correcting pathological configurations of segments of the lower extremities containing, in a given set, the adjustable pelvic belt, the means for centering the femoral head, and the means for holding the thigh in a given position, general view, according to the invention.

In this constructive version, the proposed modular exoskeleton contains adjustable pelvic belt 47 (FIG. 15) positioned around the pelvic area of the user and having base 48, on each of the opposite ends of which means 49 for centering the femoral head is secured, executed with a possibility of fixing the position of the thigh in the hip socket. The device contains two adjustable thigh cuffs 50, each of which is suitable for placement around the corresponding distal part of the user's thigh and executed with a possibility of turning in the sagittal plane. On each thigh cuff 50, the corresponding means 51 for holding the thigh in a given position is secured, each of which is secured with a possibility of positioning rotation in the horizontal plane, and two first rods 52. Each first rod 52 is fastened, with its first end, to means for fastening the first end of the first rod (not shown in the drawing) secured in the corresponding means 49 for centering the femoral head, and its other end is connected to means 51 for holding the thigh in a given position executed with a possibility of positioning rotation in the horizontal plane.

Each first rod 52 is made in the form of a pivot with a complex three-dimensional shape, having its first straight-line segment 53 oriented along the rotation axis of first rod 52, its second straight-line segment 54 essentially oriented along the user's tibia, and its third curvilinear segment 55 smoothly connecting first and second straight-line segments 53, 54.

The length of straight-line segments 53, 54 of first rod 52 corresponds to anthropomorphic parameters of the user and has at least three standard sizes defining the total length of each first rod 52; however, in the described version of the execution of the apparatus, an additional means for adjusting the length of first rod 52 is provided for, which is discussed below.

At the opposite ends of base 48 of adjustable pelvic belt 47, there are landing sites 56 (FIGS. 16, 17), on each of which the first ring-like ridged surface is executed and, with a possibility of positioning free movement, means 49 for centering the femoral head of the corresponding thigh is secured.

Each means 49 for centering the femoral head of the corresponding thigh contains body 57, bevel-edged nut 58, and means 59 for fastening the first end of the first rod. On the surface of body 57 facing base 48, the second ring-like ridged surface is executed. The bevel angle of bevel-edged nut 58 is in the range from 3° to 30°. Bevel-edged nut 58 is positioned between base 48 in the zone of landing site 56 and body 57 with a possibility of positioning rotation. Moreover, means 59 for fastening the first end of first rod 52 is executed with a possibility of free rotation and linear positioning movement of the first end of first rod 52.

On butt-ends of bevel-edged nut 58, the third and the fourth ring-like ridged surfaces are executed reciprocal to the first and second ring-like ridged surfaces, respectively. Bevel-edged nut 58 is positioned between base 48 and body 57 with a possibility of entering interlocking of the third and the fourth ring-like ridged surfaces of nut 58 with the first and the second ridged surfaces, respectively, and with a possibility of positioning rotation in the plane of base 48.

Figure 18:
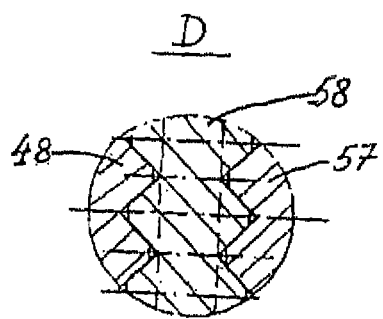
FIG. 18—fragment D in FIG. 17, enlarged scale, according to the invention.

FIG. 18 shows, in a larger scale, entering into interlocking of the above-mentioned corresponding ridged surfaces.

Figure 16:
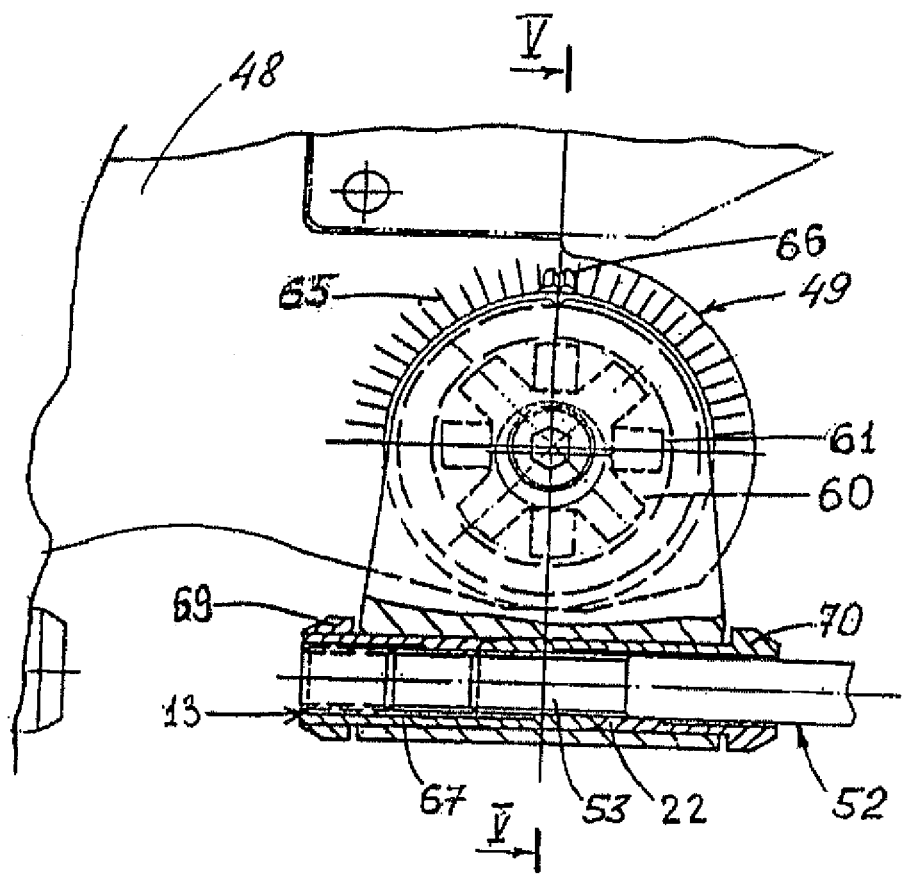
FIG. 16—a fragment of the adjustable pelvic belt with the means for centering the femoral head, according to the invention.
Figure 17:
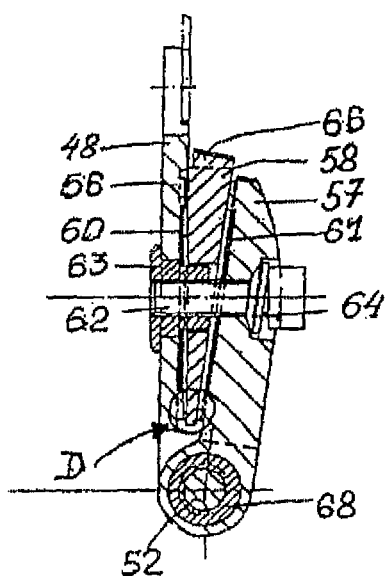
FIG. 17—section along line V-V in FIG. 16.

Each means 49 for centering the femoral head contains first flat spring 60 positioned between juxtaposed surfaces of base 48 and bevel-edged nut 58 inside the first and the third ring-like ridged surfaces, respectively. Moreover, it also contains second flat spring 61 positioned between juxtaposed surfaces of body 57 and bevel-edged nut 58 inside the second and the fourth ring-like ridged surfaces, respectively. In FIG. 16, dashed lines indicate the first and the second flat springs 60, 61 having a cross-shaped leaf configuration, as well as the borders of said ridged surfaces.

Body 57, bevel-edged nut 58, and first and second flat springs 60, 61 are fastened on base 48 using bolt 62, one end of which is positioned in insert 63 positioned in base 48 and partially in bevel-edged nut 58. On the other end of bolt 62 there is head 64, the shape of which is adapted for convenient turning of bolt 62.

Means 49 for centering the femoral head, executed as described above, is fairly compact and protrudes to an insignificant extent above base 48, which does not cause inconvenience to the user while wearing the device being patented.

Each bevel-edged nut 58 is executed with a possibility of discrete positioning rotation and on the surface of base 48, around the first ring-like ridged surface, there is scale 65 the unit of which corresponds to the step of discrete positioning turn of bevel-edged nut 58. To visualize the installation position of bevel-edged nut 58, it features protrusion 66.

Inside body 57 of means 49 for centering the femoral head, the eighth through channel is made that is oriented along base 48. In the eighth through channel, means 59 for securing the first end of first rod 52 is placed, executed with a possibility of free rotation and linear positioning movement of first rod 52.

In the described version, means 59 for securing the first end of first rod 52 contains first and second inserts 67, 68 with corresponding flanges 69, 70, positioned with a possibility of linear movement in the eighth through channel of body 57 from the opposing sides with a possibility of free rotation relative to this body 57. Each insert 67, 68 is threaded on its inner surface, wherein threading on first insert 67 is in the opposite direction relative to threading on second insert 68. Inside inserts 67, 68, the first end of first rod 52 is positioned, on the outer surface of which there is threading. The first end of first rod 52 together with inserts 67, 68 comprise a threaded assembly ensuring linear positioning movement of first rod 52. Moreover, during rotation of inserts 67, 68 by means of oppositely directed threading the first end of first rod 52 moves linearly in one direction or the other, which allows adaptation of first rod 52 for a given user.

FIG. 16 shows several positions of first straight-line segment 53 of first rod 52 inside inserts 67, 68, illustrating the possibility of linear positioning movements.

Each means 51 for holding the thigh in a given position is secured on adjustable cuff 50 and executed with a possibility of positioning rotation in the horizontal plane. In the described version of the apparatus, each means 51 for holding the thigh in a given position contains hollow body 71 (FIGS. 19, 20) and fastening unit 72 that is secured from one side of body 71 partially inside of it and fastened on axle 73 on adjustable thigh cuff 50 with a possibility of hip rotation in the static position and during movement. From the opposite side of hollow body 71, the second end of first rod 52 is positioned that is secured with a possibility of linear movements. Lid 75 is secured on the butt-end of body 71 using bolts 74, through which the second end of first rod 52 is passed. For smooth movement of first rod 52 inside body 71, inserts 76, 77 are placed on the end of first rod 52 and in body 71 in the zone of lid 75 that are made of resilient material, for example fluorine plastic.

Fastening unit 72 contains insert 78 fastened in hollow body 71 and having tailpiece 79 protruding from the body, in which a ball bearing is placed having stator 80 fastened in tailpiece 79, and rotor 81 in the shape of a spherical belt firmly secured on axle 73 and executed with a possibility of rotation in the sagittal and horizontal planes. Insert 78 is executed as an assembled unit and comprises two parts connected with each other using, for example, rivet 82.

Means 51 for holding the thigh in a given position, executed as described above, is used in the apparatus being patented in cases when the user has pathological configurations of the thigh.

In cases when it is necessary to carry out additional correction of the position of the tibia and/or the foot of the user, the apparatus must be additionally equipped with means for rotating the tibia and/or means for holding the tibia in a given position, and/or means for correcting the position of the foot and the movement range thereof in the talocrural joint.

Figure 19:
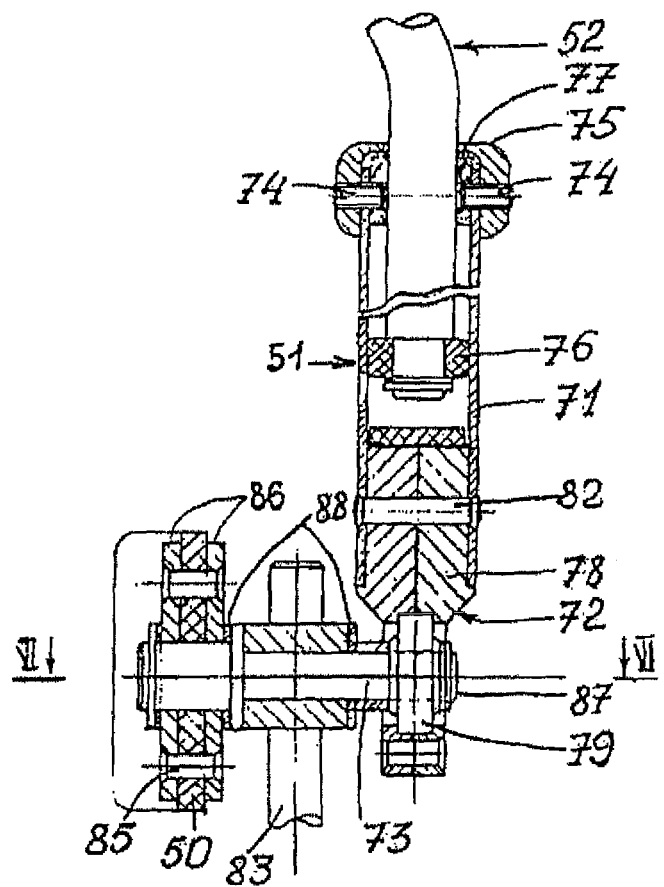
FIG. 19—the means for holding the thigh in a given position, longitudinal section, according to the invention.
Figure 20:
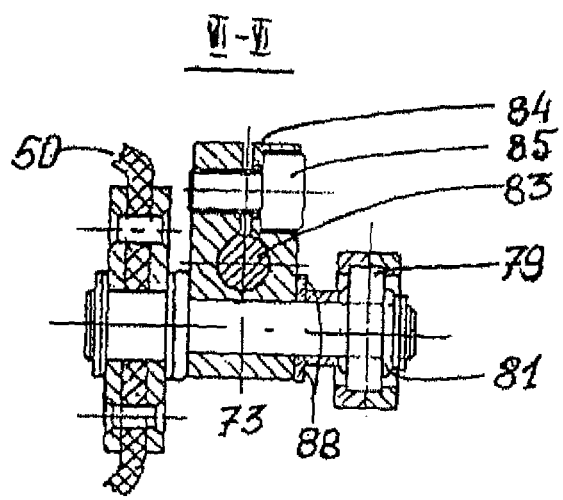
FIG. 20—section along line VI-VI in FIG. 19.

To connect means 51 for holding the thigh in a given position with the device following it along the length of the user's lower extremity, for example, with means for rotating the tibia, second rod 83 is provided. Unit 84 for fastening the first end of second rod 83 is shown in FIGS. 19, 20.

In cases when the apparatus is meant for correcting the configuration of just the hip of the user, second rod 83 is absent and thus said fastening unit 84 is absent. To facilitate understanding of the drawings, FIGS. 19, 20 depict one version of the above-mentioned construction of the apparatus, specifically the version with the presence of said unit 84 for fastening the first end of second rod 83.

On axle 73 on adjustable thigh cuff 50, with a possibility of rotation in the sagittal plane, unit 84 for fastening the first end of second rod 83 is placed, body $84_1$ of which has the ninth through channel in which, with a possibility of rotation and linear positioning movement, the first end of second rod 83 is secured. For convenience of assembly, body $84_1$ of unit 84 comprises two parts connected using bolt 85.

To convey firmness to adjustable thigh cuff 50, metallic nuts 86 are provided that are firmly secured from the opposite sides of cuff 50 using rivets 82. The ends of axle 73 are secured with a possibility of free rotation on adjustable thigh cuff 50 and on inserts 78 of means 51 for holding the thigh in a given position, for example, using bolt 87 securing axle 73. To avoid interlocking of unit 84 for fastening the first end of second rod 83 with thigh cuff 50 and the bearing, nuts 88 are placed between them that are made of, for example, fluorine plastic.

Figure 21:
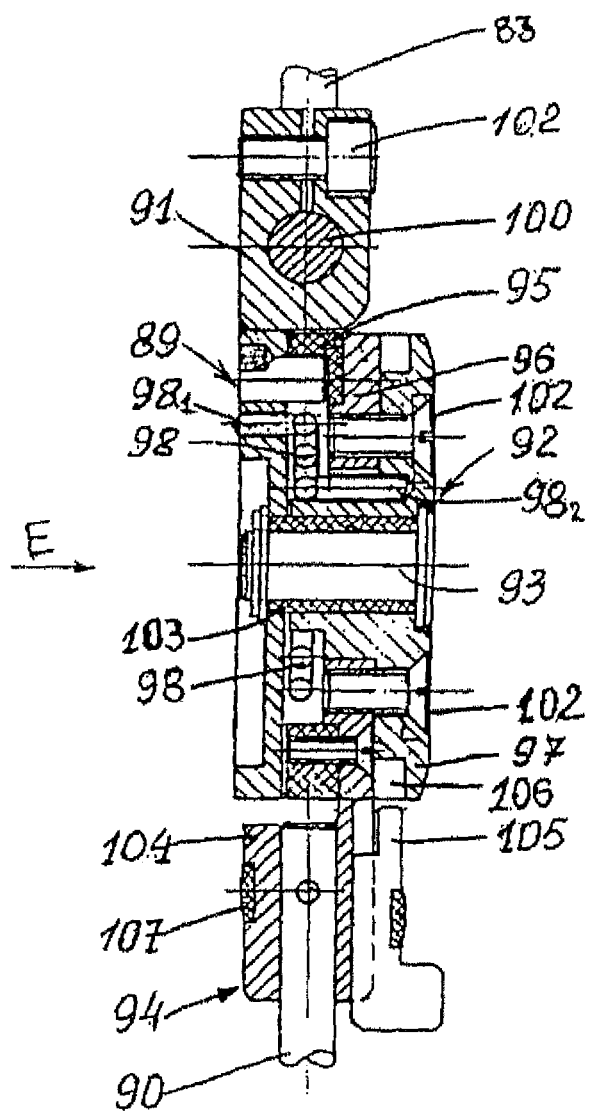
FIG. 21—the means for rotating the tibia, longitudinal section, according to the invention.
Figure 22:
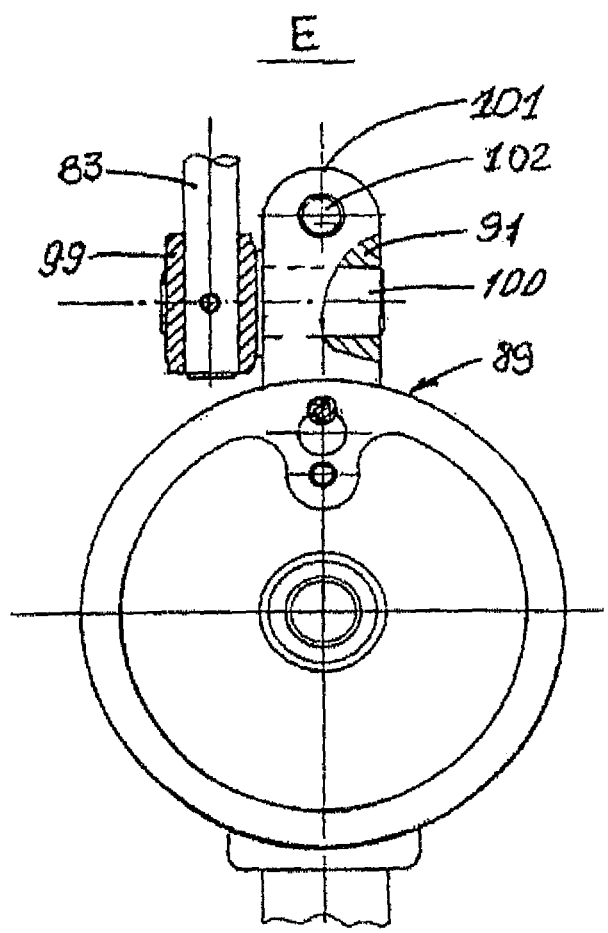
FIG. 22—view along arrow E in FIG. 21.

The modular exoskeleton contains at least one means 89 (FIGS. 21, 22) for rotating the tibia, executed with a possibility of correcting the position of the rotation axis of the knee joint in the frontal and horizontal planes, at least one means for holding the tibia in a given position (shown in FIGS. 23, 24, and will be described below) executed with a possibility of rotating the foot in the horizontal plane, at least one second rod 83, and at least one third rod 90 connecting means 89 for rotating the tibia with means 51 for holding the thigh in a given position and the means for holding the tibia, respectively.

In the described version of the proposed modular exoskeleton, means 89 for rotating the tibia contains stepped body 91, in the second step of which knee hinge 92 is mounted that is executed with a possibility of limited rotation in the sagittal plane relative to axle 93 of knee hinge 92. Axle 93 is fastened with its ends in stepped body 91 and in knee hinge 92. The second end of second rod 83 is fastened in the first step of stepped body 91 and is executed with a possibility of positioning rotation in the frontal and horizontal planes. The first end of third rod 90 is positioned in unit 94 for fastening the first end of third rod 90 connected to knee hinge 92.

In the described version, means 89 for rotating the tibia contains insert 95 positioned between base 96 of knee hinge 92 and the second step of stepped body 91, made of a resilient material, for example rubber. In the present construction, insert 95 is C-shaped for convenience of its placement in stepped body 91.

Knee hinge 92 contains base 96 abutting insert 95, lid 97 executed with a possibility of discrete positioning rotation and fixation in a given position, and spring 98 with its first end $98_1$ fastened to the second step of stepped body 91, and its other end $98_2$ fastened to lid 97 of knee hinge 92 and executed with a possibility of limiting rotation of knee hinge 92.

The second end of second rod 83 is fastened to the first step of stepped body 91 by collar 99 that is positioned on axle 100 which, with a possibility of rotation, is fastened in protrusion 101 of stepped body 91. Protrusion 101 of stepped body 91 is executed as an assembled unit held together using a fastening element, for example bolt 102.

Lid 97 is connected to base 96 using fastening elements, in this case bolts 102. To achieve a more smooth and obstacle-free rotation, axle 93 of knee hinge 92 is positioned in insert 103 made of, for example, fluorine plastic.

In the described version, unit 94 for fastening the first end of third rod 90 contains collar 104 that is fastened on base 96 of knee hinge 92, and lock 105 executed with a possibility of interlocking with lid 97 of knee hinge 92. Along the periphery of lid 97 from the side facing base 96, there is a set of discretely positioned slots 106 intended for interacting with lock 105 and ensuring discrete positioning rotation of lid 97 of knee hinge 92 in order to achieve a given position. In the described version, lock 105 comprises a latch (lift latch). For a more secure fixation of the position of the latch, clamping element 107 is provided that wraps around collar 104 and lock 105 and comprises, in the described version, a baffle made of rubber, for example.

Figure 25:
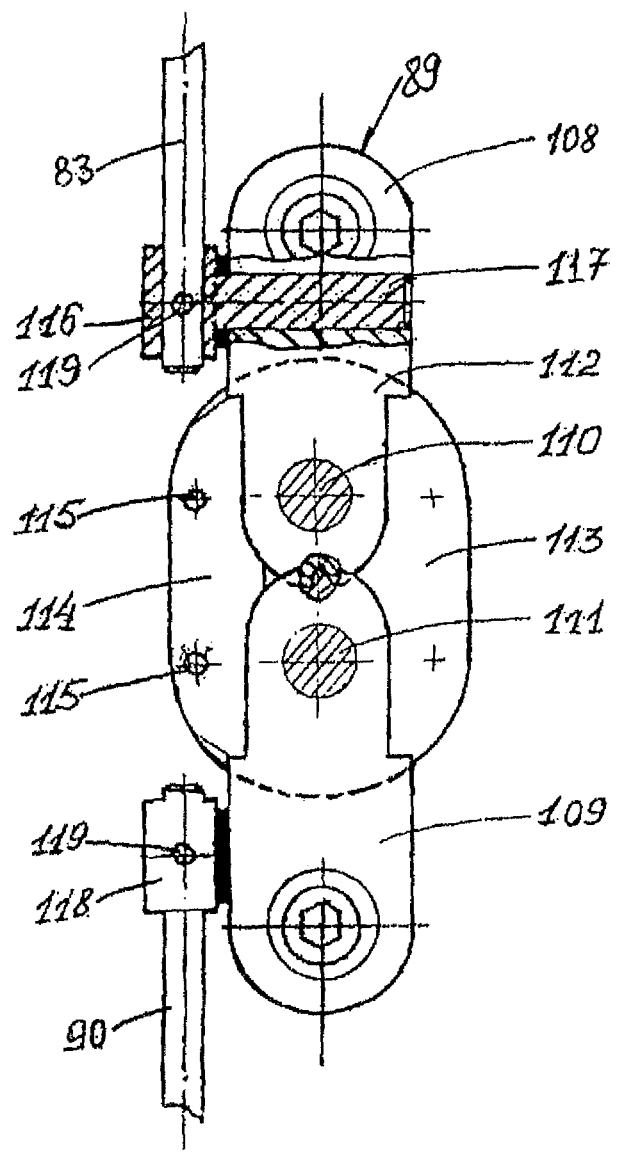
FIG. 25—the means for rotating the tibia, longitudinal section, as another version of its execution, according to the invention.

In another version, means 89 (FIG. 25) for rotating the tibia contains a toothed pair executed with a possibility of limited rotation in the sagittal plane and containing first and second gears 108, 109, each of which has toothed rim $108_1$, $109_1$, rotation axle 110, 111, and the first and the second side plates 112, respectively (one plate 112 is not installed in the drawing), positioned from the butt-ends of the toothed pair. Side plates 112 protect gears 108, 109 from clothes, foreign objects, or the user's upper extremities getting caught in them, particularly important when the apparatus is used in children.

Front and back stops 113, 114 are positioned between side plates 112, secured on one of the side plates 112 and preventing excessive extension and flexion of means 89 for rotating the tibia, respectively. Side plates 112 have a certain constructive purpose, i.e. they help assemble gears 108, 109 into a single unit using axles 110, 111 passing through first and second gears 108, 109 and fastened on the respective side plates 112 using bolts 115.

In the described version of means 89 for rotating the tibia, fastening of the second end of second rod 83 and the first end of third rod 90 is executed analogously: the second end of second rod 83 is fastened in first gear 108 with a possibility of positioning rotation in the frontal and horizontal planes using collar 116 positioned on axle 117. Moreover, the first end of third rod 90 is fastened in second gear 109 with a possibility of positioning rotation in the frontal and horizontal planes using collar 118 positioned on the axle (not shown in the drawing). The lengths of second rod 83 and third rod 90 are fixed using fastening elements, for example bolts 119, 120.

The described versions of means 89 for rotating the tibia allow correction of the position of the tibia in the horizontal and frontal planes while simultaneously performing given flexion and extension of the tibia during walking.

Figure 23:
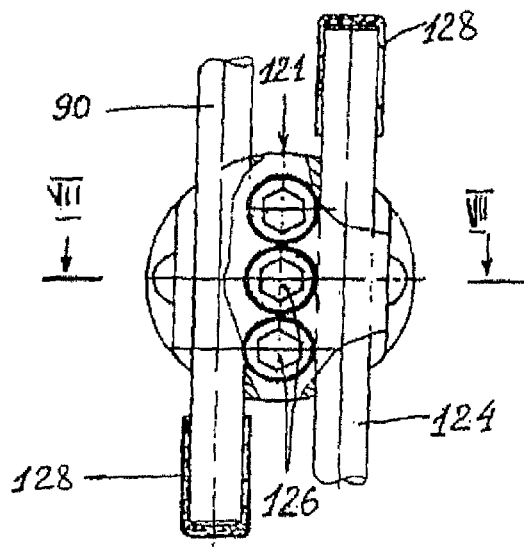
FIG. 23—the means for holding the tibia in a given position, general view, according to the invention.
Figure 24:
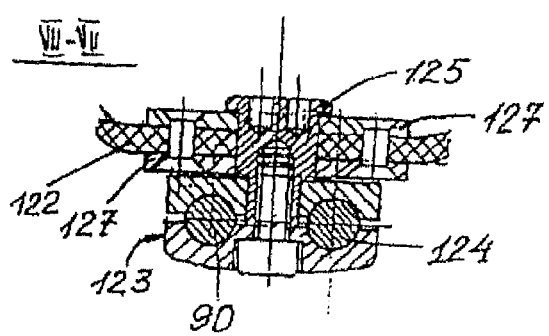
FIG. 24—section along line VII-VII in FIG. 23.

As was noted above, the apparatus contains means 121 for holding the tibia in a given position, shown in FIGS. 23, 24.

In the described version of the apparatus, means 121 for holding the tibia in a given position contains adjustable calf cuff 122 (FIG. 24) and base 123 having the tenth and the eleventh through channels in which, with a possibility of linear positioning movement, the second end of third rod 90 and the first end of fourth rod 124 are fastened, respectively. Base 123 is fastened on axle 125 with a possibility of rotation in the sagittal plane, and axle 125 is fastened on adjustable calf cuff 122.

For convenience of placement of third and fourth rods 90, 124, base 123 is executed as a composite; moreover, the parts comprising base 123 are connected to one another using a bolt connection comprising three bolts 126 (FIG. 23). Axle 125 is executed as stepped and fastened on calf cuff 122 by its large base. To convey firmness along both sides of cuff 122, metallic nuts 127 are placed. Fastening of nuts 127 to cuff 122 is achieved using rivets 128. There are protective caps 129 on the ends of third and fourth rods 90, 124.

Figure 26:
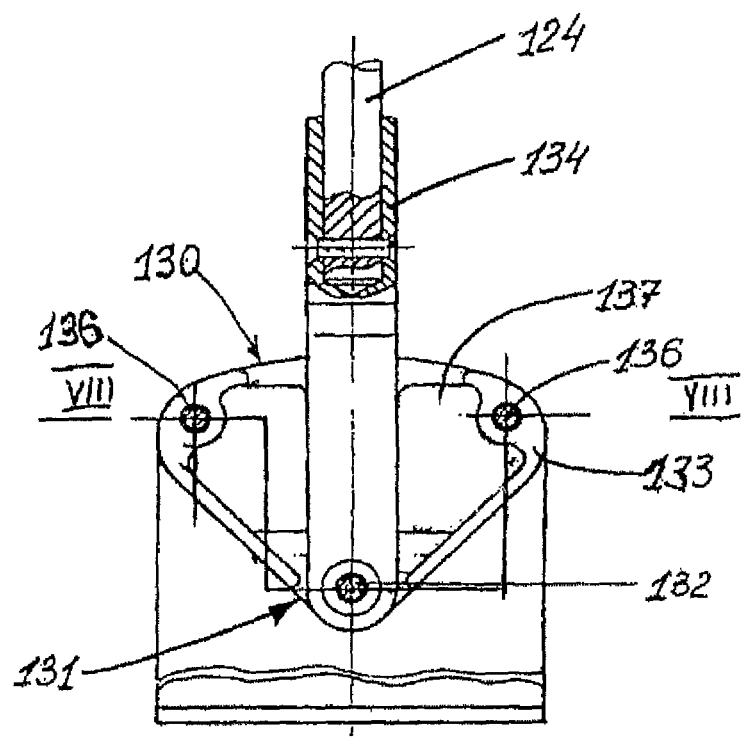
FIG. 26—the means for holding the foot relative to the talocrural joint and correcting the movement range thereof, longitudinal section with cutaways, according to the invention.
Figure 27:
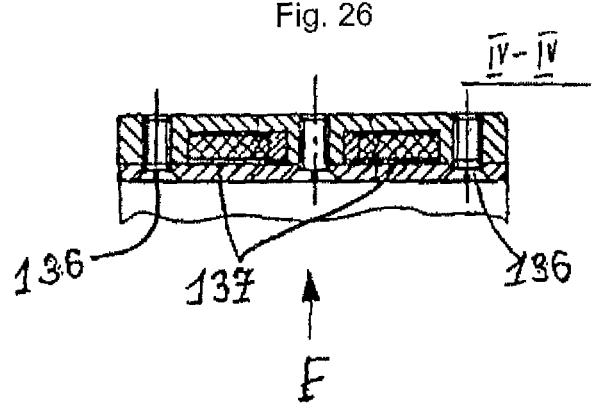
FIG. 27—section along line VIII-VIII in FIG. 26.
Figure 28:
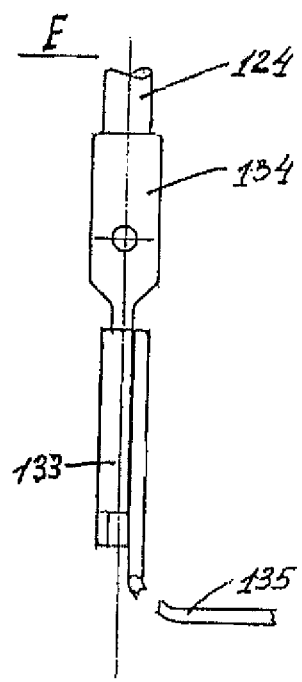
FIG. 28—view along arrow F in FIG. 27.

In the described version, means 130 for correcting the position of the foot and the movement range thereof in the talocrural joint (FIGS. 26, 27, 28) contains outer talocrural hinge 131 having axle 132, and hollow body 133 in which tip 134 is positioned. The second end of fourth rod 124 is fastened on the first end of tip 134, and the second end of tip 134 is fastened on axle 132 of outer talocrural hinge 131 with a possibility of rotation in the sagittal plane.

The modular exoskeleton contains bent connective plate 135 with its one end fastened to axle 132 of outer talocrural hinge 131 with a possibility of rotation in the sagittal plane, and its other end—to means for accommodating the foot (not shown in the drawing).

Hollow body 133 of means 130 for correcting the position of the foot and the movement range thereof in the talocrural joint is executed as a composite and held together using connecting elements, for example bolts 136. In hollow body 133 at least one spring element 137 is positioned that is executed with a possibility of limiting rotation of the foot in the sagittal plane.

In the described version, two spring elements 137 are positioned in hollow body 133 that fill the inner volume of hollow body 133 and are executed with a possibility of limiting rotation of the foot in the sagittal plane. Spring elements 137 create more favorable conditions for using the apparatus and are made, for example, of latex or rubber.

Figure 29:
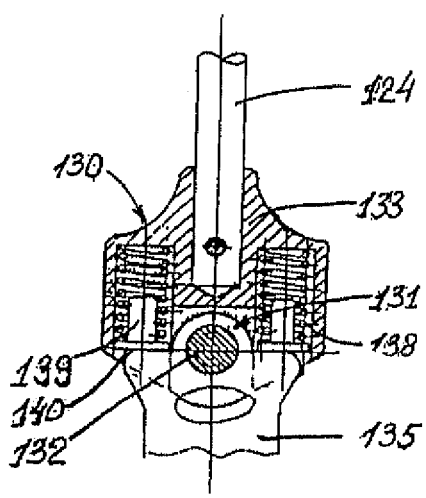
FIG. 29—the means for holding relative to the talocrural joint and correcting the movement range thereof, longitudinal section, as another version of its execution, according to the invention.

In another version of the proposed apparatus, means 130 (FIG. 29) for correcting the position of the foot and the movement range thereof in the talocrural joint contains outer talocrural hinge 131 having axle 132 and body 133 in which the second end of fourth rod 124 is secured.

The modular exoskeleton contains bent connecting plate 135 that is spring-assisted to body 133 using springs 138, inside each of which cog 139 is located that is positioned on supporting plane 140 interacting with connecting plate 135 on its periphery. One end of connecting plate 135 is fastened on axle 132 of outer talocrural hinge 131 with a possibility of rotation in the sagittal plane, and the other end is fastened on means for accommodating the foot (not shown in the drawing).

In cases when, in the process of using the apparatus being patented, the user's calf volume changes substantially along its length, which is particularly important for children during the period of active growth, it is difficult to secure tight fit of third and fourth rods 90, 124 to the tibia and secure positioning of calf cuff 122 using only one adjustable calf cuff 122. In such a case, the apparatus contains two adjustable calf cuffs 122$_1$ and 122$_2$, and means 121 for holding the tibia in a given position comprises two analogously executed parts 121$_1$ and 121$_2$, positioned in the upper and lower parts of the calf and connected using intermediate rod 141 (FIG. 30 (*a,b*)), which precludes tilting and poor fit. The version of the proposed apparatus shown in FIG. 30 (*a,b*) will be described in more detail below.

Each part 121$_1$ and 121$_2$ of means 121 for holding the tibia in a given position is executed analogously as described above (FIGS. 23, 24).

Figure 30:
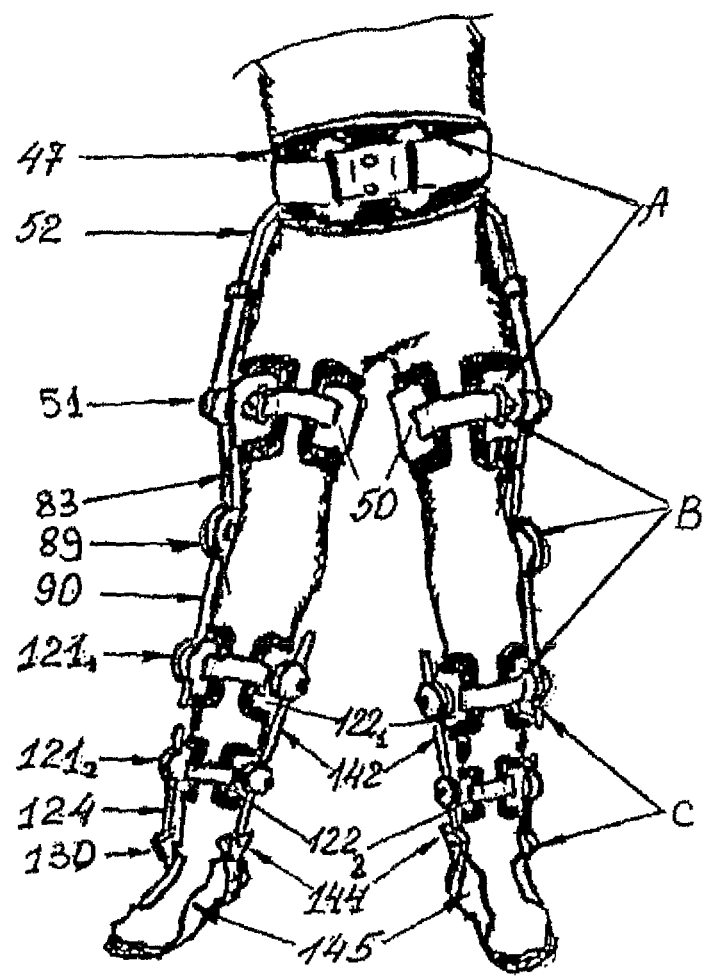
FIG. 30 (*a, b*)—same as FIG. 15, in a set, comprising the means for rotating the tibia, the means for holding the tibia in a given position, the means for holding the foot relative to the talocrural joint and correcting the movement range thereof, and the means for accommodating the foot, front and rear view, respectively, according to the invention.
Figure 30:
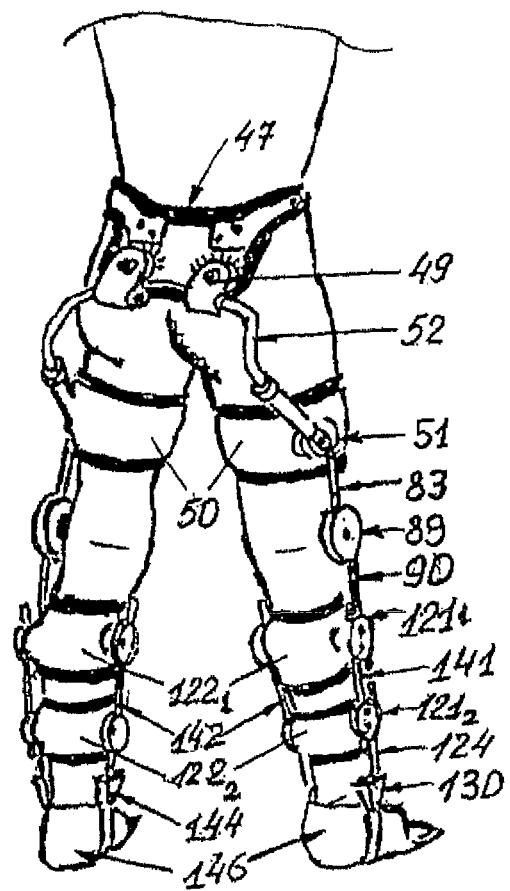

To achieve a more secure fixation of the user's tibia in a given position, the apparatus contains at least one second intermediate rod 142 (FIG. 30 (*a,b*)) positioned on the inner side of the user's calf and fastened to adjustable calf cuffs 122$_1$ and 122$_2$.

Figure 31:
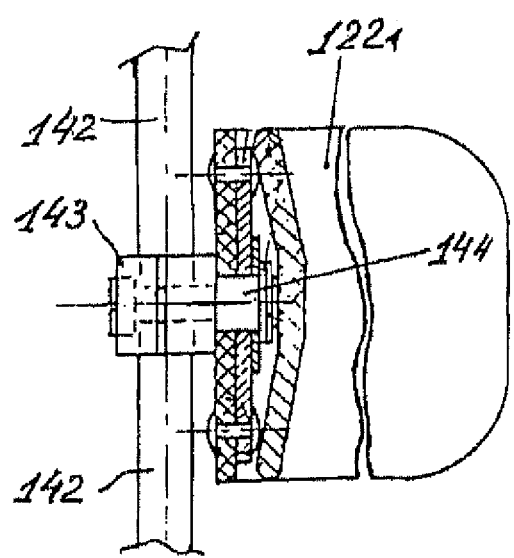
FIG. 31—the unit of fastening of the second intermediate rod, with cutaway, according to the invention.

Fastening of second intermediate rod 142 is achieved using two collars 143 (first and second) (FIG. 31), each of which is positioned on axle 144 fastened with a possibility of rotation in the sagittal plane on the corresponding calf cuff, for example cuff 122$_1$, as shown in FIG. 31.

The first end of second intermediate rod 142 is secured, with a possibility of linear positioning movements, in first collar 143 and the second end of rod 142 is passed through second collar 143 and connected to inner talocrural hinge 145 of means 130 for holding the foot relative to the talocrural joint and correcting the movement range thereof.

Inner talocrural hinge 145 is executed analogously to the above-described versions of executing outer talocrural hinge 131 (FIG. 26-29), and because of that it is not shown in detail in the accompanying drawings.

In one version, inner talocrural hinge 145 has a hollow body in which a tip is located, on one end of which said second end of the second intermediate rod is located, and the other end of the tip is fastened on the axle of said inner talocrural hinge 145 with a possibility of rotation in the sagittal plane; moreover, the device contains a bent connecting plate with its one end fastened to the axle of said inner talocrural hinge 145 with a possibility of rotation in the sag ittal plane, and the other end fastened to said means for accommodating the foot.

In another version, inner talocrural hinge 145 has a body in which said second end of the second intermediate rod is fastened; moreover, the device contains a bent connecting plate spring-assisted to said body with its one end fastened to the axle of said inner talocrural hinge 145 with a possibility of rotation in the sagittal plane, and the other end fastened to said means for accommodating the foot.

FIG. 30 (*a,b*) shows a version of the modular exoskeleton being patented as a complete set, comprising pelvic belt 47 with means 49 for centering the femoral head; means 51 for holding the thigh in a given position; means 89 for rotating the tibia; means 121 for holding the tibia in a given position; means 130 for correcting the position of the foot and the movement range thereof in the talocrural joint; and means 146 for accommodating the foot. Moreover, pelvic belt 47 with means 49 for centering the femoral head and means 51 for holding the thigh in a given position comprise first module A. Means 51 for holding the thigh in a given position, means 89 for rotating the tibia, and means 121 for holding the tibia in a given position comprise second module B. Means 121 for holding the tibia in a given position and means 130 for correcting the position of the foot and the movement range thereof in the talocrural joint comprise third module C.

First, second, third, fourth rods 52, 83, 90, 124 and first and second intermediate rods 141, 142 serve as connecting elements and, essentially, each of which comprises a cylindrical rod executed with a possibility of linear positioning movement and/or rotation and/or free linear movement, as was mentioned above.

The device being patented is characterized by its modular nature, i.e. the possibility of correcting pathological configurations of various segments of the lower extremities using separate modules A, B, C or their combinations, or the entire modular exoskeleton.

We will examine in more detail the practicability of using the above-named modules and means depending on various pathological configurations of the lower extremities.

When the user has a pathological configuration of the thigh in one lower extremity, when there is inner rotation of the thigh or thigh adduction, the proposed device comprises first module A containing adjustable pelvic belt 47 with means 49 for centering the femoral head in the hip socket, and means 49 for holding the thigh in a given position, that are connected using first rod 52 executed with a possibility of rotation and free linear movement.

When the user has varus or valgus positioning of the tibia in one lower extremity, the proposed device comprises second module B containing means 51 for holding the thigh in a given position, means 89 for rotating the tibia, and means 121 for holding the tibia in a given position, that are connected using second and third rods 83, 90, respectively. Moreover, rod 83 is executed with a possibility of rotation and linear positioning movement, and third rod 90 is executed with a possibility of linear positioning movement. Above-named means 51, 89, 121 (i.e. second module B) ensure the possibility of changing the position of the tibia in the horizontal and frontal planes.

If the user has adduction or abduction of the foot in one lower extremity, the proposed device comprises third module C containing means 121 for holding the tibia in a given position and means 130 for correcting the position of the foot and the movement range thereof in the talocrural joint, connected using fourth rod 124 executed with a possibility of linear positioning movement. Above-named means 121 and 130 (i.e. third module C) ensure the possibility of changing the position of the tibia and the foot in the horizontal plane. To achieve the best outcome when using the proposed device when the user has equine positioning of the foot or foot adduction or abduction, better results can be obtained by using all said modules A, B, C containing all said elements and means 47, 49, 51, 89, 121, and 130.

Before using the modular exoskeleton, an apparatus of the appropriate size is selected for a given user. Mainly apparatuses of three sizes are used, whereby there is a possibility of regulating separate modules lengthwise by defining the length of separate connecting rods.

We will examine the assembly of the proposed modular exoskeleton on the user wherein it contains the modules, element, and means mentioned above on both lower extremities of the user.

Firstly, calf cuffs $122_1$ and $122_2$ and means 130 for correcting the position of the foot and the movement range thereof in the talocrural joint are put on, and the lengths of rods 90, 141, 142, and 124 are set so that axle 93 of means 89 for rotating the knee joint is projected a bit higher (approximately by 2 cm) relative to the knee joint's cavity.

Subsequently, adjustable pelvic belt 47 (FIG. 15) is put on the user's pelvic area, securing its tight fit with the user's body. Then, the user's thighs are placed into thigh cuffs 50 that are secured in the lower third of the thigh so that these cuffs 50 do not end up under knee joints, after which the length of second rod 83 is set.

After the user puts on the modular exoskeleton and the lengths of said rods 90, 141, 142, 124 are set, means 49 for centering the femoral head, means 89 for rotating the tibia, and means 130 for correcting the position of the foot and the movement range thereof in the talocrural joint are set out in such a position of the corresponding means 49, 89, 130 as to achieve correction of the position of the rotation axes of the hip, knee, and talocrural joints in the horizontal and frontal planes.

For correcting the position of the rotation axis of the hip joint, means 49 for centering the femoral head (FIGS. 16, 17, 18) is situated in mid-position at which the axis of first rod 52 is parallel to the longitudinal axis of base 48.

In this position, hips' abduction in the positions "sitting" and "standing" proceeds with the same abduction angles.

By turning means 49 for centering the femoral head with first rod 52 in the horizontal plane, various angles of abduction in the position "sitting" and the position "standing" are secured.

Using approximation methodology, the optimal direction of the axis of the corresponding first rod 52 is selected, and the position of the corresponding means 49 for centering the femoral head is fixed by bolt connection. Such a position of means 49 for centering the femoral head and first rod 52 connected thereto corresponds to the prescribed correction of the thigh and does not cause painful sensations to the user.

If necessary, the proposed modular exoskeleton can be custom adjusted for each hip joint of a given user, which favorably distinguishes it from known constructions of analogous utility.

To correct the position of the rotation axis of the knee joint in the horizontal plane, tightening of two bolts 102 (FIG. 21) of means 89 for rotating the tibia that hold the position on the second end of second rod 83 is loosened, and means 89 for rotating the tibia is turned in the horizontal plane together with the user's lower extremity. Subsequently, the lower extremity is held in the selected position and bolts 102 are tightened.

To correct the position of the rotation axis of the knee joint in the frontal plane, tightening of bolt 102 of means 89 for rotating the knee joint is loosened, third rod 90 is dislodged and held in a selected position together with the user's tibia, and the position of the tibia is fixed by tightening bolt 102.

To correct the position of the rotation axis of the talocrural joint in the horizontal plane, tightening of the bolts 102 (FIGS. 21, 22) on base 96 is loosened, the user's foo, is turned together with means 146 for accommodating the foot in the desired direction by rotating the first end of fourth rod 124 in the eleventh through channel, and the foot is held and fixed in the corrected position by tightening bolts 102 on base 96.

Because the exoskeleton being patented features a simple compact construction, it can be used together with other devices that allow solving of the problem of correcting pathological configurations of the lower extremities, especially in children.

As was already described earlier, the proposed exoskeleton comprises separate modules A, B, C (the components of said modules are described above) which, if necessary, can be used independently, in various combinations, or all together.

In the version of the modular exoskeleton shown in FIG. 30 (*a, b*), all said modules A, B, C containing said elements and means 47, 49, 51, 89, 121, 130, 146 are put on both lower extremities of the user. However, said modules A, B, C containing said elements and means 47, 49, 51, 89, 121, 130, 146 can be put on, if medically necessary, on one or both lower extremities of the user all together as well as in various combinations.

Thus, the modular exoskeleton being patented provides for the possibility to carry out the correction of pathological configurations of all segments of the lower extremities, and in this case comprises all above elements and means 47, 49, 51, 89, 121, 130, 146 connected to one another by corresponding rods 52, 83, 90, 124, 141, 142, and it also provides for the possibility to carry out the correction of pathological configurations of separate segments of the lower extremities or combinations of pathological configurations of the lower extremities and, in this case, comprises separate above-listed elements and means, connected to one another by the corresponding rods.

Below we provide specific examples of using the method being patented, and the device for correcting pathological configurations of segments of the lower extremities in users of various ages.

EXAMPLE 1

User N. R., age: 8.

Diagnosis: infantile cerebral palsy (thereafter ICP), spastic diplegia predominantly affecting the right extremities, severe form, adductor-prone positioning of the thighs, pathological flexion and valgus positioning of the tibias, more on the right, abductor-equine-planovalgus positioning of the feet.

On examination: the user does not stand or walk without assistance. Patient walks while supported on one arm or while leaning on two Canadian crutches in the position of triple bending with inner rotation of the thighs and leaning on front-inner regions of the feet. During walking, there is non-permanent crossing of lower extremities at the level of the lower third of the thigh. There is pronounced valgus positioning of the right tibia in the position "standing" and during locomotion; valgus positioning of the left tibia is less pronounced. In the position "standing" and during locomotion, there is notable pathological abduction of the feet, more so of the right foot.

The user underwent the step-by-step correction of the longitudinal axes of the right and the left lower extremities with application of the proposed method and device over a period of one year.

For each lower extremity, the proposed exoskeleton was used comprising three modules (A, B, C); moreover, a spring-assisted mechanism was used in the knee hinge joint of module B for each lower extremity ensuring limitation of pathological flexion of the thigh during support at locomotion. In the boot of module C for each foot, correcting inserts were used for orthopedic correction of the medial longitudinal arch and high inner support of each foot. Module C of the exoskeleton being patented contained outer and inner talocrural joint hinges for each lower extremity, ensuring improved stabilization of the corrected position of each foot.

The proposed method was utilized including correction of said pathological configurations of said segments of both lower extremities, using the exoskeleton being patented. Said correction comprised four-step correction of the position of the longitudinal axes of said segments. To do this, the step-by-step adjustment of the exoskeleton's constructive elements was carried out four times in the course of a year with consideration of the dynamics of muscle tone and the user's growth, the degree to which the user adapted to the corrected position of segments of the lower extremities during each step of using the described method, and the step-by-step elimination of the imbalance of forces in the muscles supporting hip, knee, and talocrural joints of both lower extremities. To eliminate the imbalance of forces in the muscles and correct the muscle tone in the setting of initial spastic flexion-pronation musculature of the user's lower extremities in the framework of the method being patented, cryocontrast methodology was utilized (contrast alternation of applying cold and heat on the so-called motor points of spastic muscles) along with stimulation of their antagonists for improving contractile ability using apparatus Compex-3, complex physical therapy for better adaptation of the user's muscles with individual selection of therapeutic-training load at each step of using the device, and methodology of kinesiological taping of muscles (Dr. Kenzo Kase, Founder) whose functional deficiency defined pathological configurations of the thigh, the tibia, and the foot of each lower extremity.

Module A of the exoskeleton for correcting adductor-prone positioning of each thigh was tuned in the step-by-step manner; moreover, abduction and outer rotation was dosed at each step for each thigh without cross-effect, depending on the severity of initial pathological configuration at each step of the correction. Module B of the exoskeleton, together with the user's tibia, was rotated in the step-by-step manner in horizontal and frontal planes. Subsequently, the corrected position was fixed simultaneously with the position of module C, by which correction of valgus positioning and inner rotation of the tibia and the resultant valgus positioning of the foot of each lower extremity was achieved without cross-effect, additionally changing the position of module C relative to the position of module B of each lower extremity to correct pathological abduction of the feet. The movement range of the talocrural hinges was set for each lower extremity with limitation of plantar flexion of the feet, but without limiting dorsiflexion, essentially in the same manner for the left and the right lower extremities.

Check-up visit after one year revealed the following: the user stands without the correcting exoskeleton and walks using two Canadian crutches; the severity of valgus positioning of the tibia, particularly left tibia, has diminished. The user engages the entire foot for support. Pathological abduction of both feet has been eliminated. Spastic severity of adductors of both sides has decreased and the range of passive thigh abduction has increased. Recommended: continue using the proposed method and device.

EXAMPLE 2

User K. K., age: 24.

Diagnosis: ICP, spastic diplegia of moderate severity predominantly affecting left extremities, secondary multi-dystrophic syndrome, adductor-prone positioning of the thighs, inner rotation of both lower extremities, valgus positioning of the left foot, pronounced equine-planovalgus positioning of the left foot.

On examination: the user walks without assistance yet with a pronounced rocking of the torso during walking, rotates the lower extremities inward with support on the entire right foot and front-inner region of the left foot. The thighs are adducted. The support phases during locomotion are not differentiated (there is no "rollover" from the heel part of the foot to the distal part of the foot during walking). In the standing position and during locomotion, moderate valgus positioning of the left tibia is evident. The right lower extremity is more supportive, the single-support period of the left lower extremity is shortened. There is notable tilt of the pelvis and torsion of the torso in the standing position and during locomotion to the left. The left lower extremity is functionally shortened by 8 mm due to pathological torsion and valgus positioning of the left tibia.

The user underwent correction of the physiological axis of a lower extremity using the method and device being patented.

The proposed exoskeleton was used comprising three modules (A, B, C) for the left lower extremity and module A for the thigh of the right lower extremity. In the boot of module C, a correcting insert was used for the left foot for orthopedic correction of inner longitudinal arch and high inner support of the left foot. Module C of the exoskeleton being patented contained outer and inner hinges of the talocrural joint for the left lower extremity to better stabilize the corrected position of the left foot, because the initial pathological equine-plantar-valgus positioning of the left foot was markedly pronounced.

The proposed method was utilized including correction of said pathological configurations of said segments of both lower extremities, using the exoskeleton being patented. Said correction comprised the step-by-step adjustment of the constructive elements of the exoskeleton; using its three modules (A, B, C for the left lower extremity), the gradual correction of pathological adduction and inner rotation of the thigh, valgus positioning and inner rotation of the left tibia, and equine-planovalgus deformity of the left foot were carried out. Using module A for the right lower extremity, the step-by-step elimination of inner rotation of the axis of the right lower extremity was carried out, exerting corrective influence on the position of the right thigh.

The correcting adjustments of the exoskeleton are analogous to those described above, in example 1. The quantity of correcting steps was five during one year. The mode of use of the exoskeleton was continuous wear while awake. Elimination of adductor-prone positioning of the left and the right thigh was carried out without cross-effect, achieving a more significant abduction of the left thigh as pathological thigh adduction was initially more pronounced on the left. Prone positioning of the thighs was corrected partially to better center the femoral heads of the left and the right thighs in the corresponding hip sockets. During each step of using the described method and immediately before each adjustment of the exoskeleton, the dosed elimination of the imbalance of forces in the muscles (spastic-rigidity) and arbitrary locomotion of proximal musculature supporting the hip joints was carried out, as well as that of musculature supporting the movement of the tibia in the knee joint. The correction was carried out manually, using nighttime medicinal laying into joint immobilizers on knee joints, and no-load joint immobilizers on talocrural joints. Electric stimulation of sacrospinal muscles, gluteus muscles, and quadriceps muscles of the left and the right thigh was carried out at rest, in the regime of normal walking cyclogram, with medicinal therapy (akatinol memantine, titrated daily dose of 40 mg for one year). To better adapt the user to adjustments of the exoskeleton, physical therapy was carried out at each step of the correction. There was no need to additionally correct the length of the left lower extremity while wearing the device.

Check-up visit after one year revealed the following: the user walks without assistance, the walking pattern in the apparatus has improved significantly, torsion of the torso and tilt of the pelvis have diminished. Static-kinetic firmness and tolerance to physical exertion have improved. The user can walk significant distances (up to 300 m) without resting. Severity of valgus positioning of the left tibia has diminished significantly. Adductor positioning of the thighs has been completely eliminated (in the apparatus), inner rotation of the lower extremities has remained, but is less severe. The passive-active movement range in the hip and the talocrural joints has increased. The duration of the single-support periods for the left and the right lower extremities are essentially the same. Recommended: continue using the method and device being patented.

EXAMPLE 3

User: A. A., age: 3.

Diagnosis: consequences of a closed craniocerebral injury, brain contusion, left-sided dissociative hemiparesis predominantly affecting the left lower extremity, abnormalities of posture in the frontal plane, flexion positioning of the left forearm, adductor-prone positioning of the left thigh, recurvation of the left tibia, adductor-equine-varus positioning of the left foot with adduction of the front region, anatomical shortening of the left lower extremity by 7 mm.

On examination: the user stands and walks without assistance. The walk is hemiparetic, non-elastic, with frontal rocking of the torso; during walking, leans on frontal-outer regions of the left foot, the phases of the left foot's support period are not differentiated. During walking, there is recurvation of the left tibia in the knee joint. Reciprocal movements of upper extremities are absent during walking. Active dorsiflexion of the left foot is absent.

The proposed exoskeleton comprising three modules (A, B, C) was used for the correction of pathological configurations of the thigh, the tibia, and the foot of the left lower extremity, and module A—for the thigh of the right lower extremity (in order to stabilize the position of the pelvic belt on the user). For the user, module C contained an outer hinge of the talocrural joint, since adductor-equine-varus positioning of the left foot could be passively and effortlessly placed in a physiologically correct position. Module C of the apparatus contained correcting inserts to lessen the severity of varus positioning of the left foot and adductor positioning of the front region of the left foot (medial arch-forming and higher lateral pronating, as well as lateral dactylar pronating).

The proposed method was utilized including correction of said pathological configurations of said segments of both lower extremities, using the exoskeleton being patented. Said correction comprised the step-by-step adjustment of the constructive elements of the exoskeleton analogously to that described above in examples 1, 2. The specific feature of exoskeleton's adjustment for the user comprised limitation of movement range in the knee hinge using a stop, in order to eliminate recurvation of the left tibia during the support period upon locomotion. The mode of use of the exoskeleton was continuous wear while awake. Additionally, a joint immobilizer was used on the left knee joint, and no-load joint immobilizer was used on the left talocrural joint at night. During the year, the correction of pathological configurations of the thigh, tibia, and foot of the lower extremity was carried out in four steps, which required dynamic correction of the apparatus's settings. There was no need to additionally compensate for the length of the left lower extremity due to its existing anatomical shortening (7 mm) while using the proposed device. Module A was set on the healthy extremity in a neutral position, without correction of the range of movement in the hip joint of the right lower extremity.

The muscle tone in the left lower extremity was initially abnormally spastic, predominantly in the hip adductors, hamstring group (i.e. knee flexors), as well as triceps muscle of the calf. The dosed elimination of the imbalance of forces in the muscles was carried out at the first step—using botulotoxin preparations (dysport injections into hip adductor muscles, soleus muscle, and both sural muscles, mainly medial sural muscle); during the subsequent steps, the correction of the muscle tone was carried out using physiological factors (cryocontrast). At each step of the correction, a specific set of physical therapy exercises was selected for the user to adapt the user to the corrected position of segments of the lower extremity.

Check-up visit after 1 year: the user walks without assistance; tolerance to physical exertion has increased, walking pattern has improved. During walking without the apparatus, severity of pathological adduction of the left thigh has decreased; recurvation of the left tibia has been eliminated. During walking, the user employs the entire foot for support from its paresis side. The user consciously controls the walk, performs elements of differentiation of the support period's phases ("rollover") using the left foot (intermittently). Frontal rocking of the torso during walking has decreased substantially. Range of active movements in the left talocrural joint has increased; modest active dorsiflexion of the foot has appeared.

EXAMPLE 4

User: P. A., age: 7.
Diagnosis: long-term aftereffects of vertebral-spinal cord injury with partial damage of the spinal cord at the level of lumbar enlargement, lower atonic paraparesis, dysfunction of pelvic organs (enuresis, encopresis). There is lumbar hyperlordosis; instability of the pelvic and knee joints; recurvation of both tibias; dropping of the front region of the feet of both lower extremities.

On examination: the user does not stand, does not walk without assistance. The user sits without assistance with the legs lowered; while sitting, kyphotic posture is noticeable. The user stands with high support or support by the pelvis; while standing, there is pronounced lordosis of the lumbar segment of the spine; hyperextension of the tibias is noticeable. The user performs step movements with support by the pelvis, predominantly afforded by preserved function of the proximal muscles, thus performing circumduction hip movements while attempting to bring forward a lower extremity. Frontal rocking of the torso is pronounced. During the support period, the user performs recurvation of the tibias. During the carryover period, there is pronounced dropping of the front region of the feet of both lower extremities.

The proposed exoskeleton was used comprising three modules (A, B, C) for the left lower extremity, and three modules (A, B, C) for the right lower extremity. Each module C contained an outer hinge of the talocruraf joint. Using the stop of the knee hinge of each module B, recurvation of the tibias during the support period was eliminated. To facilitate swing movements of the tibia during the carryover period and improve support ability of the lower extremities and support at incline, the knee hinge of each module B was additionally fitted with a spring-supported mechanism.

The proposed method was utilized including correction of said pathological configurations of said segments of both lower extremities, using the exoskeleton being patented. During said correction, the step-by-step adjustment of the exoskeleton's constructive elements was performed analogously to that described above in examples 1, 2, 3. Additionally, the dosed elimination of the imbalance of forces in the muscles was carried out at initial decrease of muscle tone in both lower extremities. Elimination of the imbalance of forces in the muscles required use of the apparatus Compex-3 in the mode of electric stimulation and improvement of muscle nourishment, complex pharmaceutical therapy (medications: neirox, cortexin, actovegin, neiromidin, elcar, cytoflavin), use of apparatus physical therapy (transcranial magnetic stimulation, transdermal electroneural stimulation, laser therapy), stimulating massage, methodologies of kinesiological taping of muscles (Dr. Kenzo Kase, Founder). At each step of the correction, the user was prescribed a set of exercises for improving voluntary motor function of the lower extremities and adaptation to the apparatus. During the year, five steps of the proposed method were carried out, for which the exoskeleton underwent adjustment five times, including once due to significant growth rate of the user.

Check-up visit after one year revealed the following: the user walks in the apparatus with support by one arm; frontal rocking of the torso has decreased; the amplitude of active flexion of the hip and the tibia has increased. Dropping of the front region of the foot during the carryover period has been eliminated (in the apparatus). Support ability of the lower extremities has improved. The user makes several unassisted steps in the apparatus.

EXAMPLE 5

User: K. E., age: 14.
Diagnosis: ICP, spastic diplegia predominantly affecting the right extremity, pathological torsion of the torso to the right, adductor-prone positioning of the thighs of both lower extremities, flexion-valgus positioning of the tibias of both lower extremities, abductor-equine-planovalgus positioning of the feet of both lower extremities. Myofascial pain syndrome.

On examination: the user stands without assistance for a short period in the position of triple bending with adduction and inner rotation of the thighs of both lower extremities, pronounced valgus positioning of the tibias of both lower extremities, more on the right, with support on anteromedial regions of the feet of both lower extremities. The user walks without assistance in a fast-moving manner with pronounced sagittal and frontal rocking of the torso, in the position of typical triple bending, with leaning on anteromedial regions of the feet; the user stops walking only while being supported.

The user was prescribed treatment comprising the use of the method and device being patented in the mode of continuous wear while awake for a period of one year.

The proposed exoskeleton was used comprising three modules (A, B, C) for each lower extremity; moreover, the knee hinge of module B for the right and the left lower extremity was fitted with a spring-supported mechanism to limit pathological flexion of the tibias during support upon locomotion. Further, to better hold the tibias in a given position, module B for each lower extremity contained two cuffs. Module C for the right and the left lower extremity contained both hinges of the talocrural joint (outer and inner) to better stabilize the feet in the corrected position.

The proposed method was utilized including correction of said pathological configurations of said segments of both lower extremities, using the exoskeleton being patented. During said correction, the step-by-step adjustment of the exoskeleton's constructive elements was performed analogously to that described above in examples 1, 2, 3. Additionally, the dosed elimination of the imbalance of forces in the muscles supporting hip, knee, and talocrural joints was used at initial spastic-rigidity of hip adductors and flexion-extension musculature of both lower extremities. The method was carried out in four steps; moreover, the exoskeleton's adjustment was done four times during the year. To eliminate the imbalance of forces in the muscles and myofascial pain, cryocontrast methodology was used along with relaxing massage, application of topical anesthetics (versatis), oscillatory and high-tone therapy (apparatuses "Hivamat" and "Hi-top," respectively). At each step following a change in the apparatus's settings to better correct pathological configurations of the thigh, tibia, and foot, the user was prescribed a set of physical therapy exercises. One sub-set of the exercises was performed while wearing the exoskeleton, and the other sub-set—immediately prior to putting on the exoskeleton. At each subsequent step, the kinesiotherapeutic load was increased.

Check-up visit after one year revealed the following: improved stato-kinetic stability and the patient's pose while standing and during locomotion. The user stands unassisted for a more prolonged period. Severity of adductor positioning of the thighs while standing and during locomotion has decreased significantly; there remains insignificant prone positioning of the thighs, more of the thigh of the right lower extremity. Valgus positioning of the tibias in the exoskeleton has been completely eliminated, and without the exoskeleton—somewhat decreased, mainly on the left. The user leans on the entire foot, does not differentiate the phases of the support period. Recommended: continue using the exoskeleton and device being patented.

INDUSTRIAL APPLICABILITY

The proposed method and device can be used for rehabilitation of pathological configurations incurred due to damage of the musculoskeletal system, or damage of the central neural system. For example, the proposed method and device can be used for correcting pathological configurations of segments of the lower extremities in children suffering from infantile cerebral palsy, patients with spinal column damage possibly exacerbated by the damage of the spinal cord, patients with complications from craniocerebral injuries and acute defects in cerebral blood flow. Moreover, the proposed method can be used in treating children with various pathological configurations of segments of the lower extremities in the setting of the imbalance of forces in the muscles, inadequacy of the joint-ligament apparatus, and pathological torsion in a setting of absence of fixed musculoskeletal contractures and pronounced bone deformities of the lower extremities.

The invention claimed is:

1. Device for correcting pathological configurations of segments of the lower extremities comprising the adjustable pelvic belt (1, 47) positioned around the user's pelvic area, at least one means (3, 51) for holding the thigh in a given position, at least one means (4, 89) for rotating the tibia, at least one means (5, 121) for holding the tibia in a given position, at least one means (6, 130) for correcting the position of the foot and the movement range thereof in the talocrural joint, and at least one means (7, 146) for accommodating the foot, and a set of connecting elements, wherein said adjustable pelvic belt (1, 47) is executed with a possibility of centering at least one femoral head; said means (3, 51) for holding the thigh in a given position is executed with a possibility of positioning rotation in the horizontal plane; said means (4, 89) for rotating the tibia is executed with a possibility of correcting the position of rotation axis of the knee joint in the frontal and horizontal planes; said means (5, 121) for holding the tibia in a given position is executed with a possibility of rotating the foot in the horizontal plane; each connecting element in said set of connecting elements essentially comprises a connecting cylindrical rod (8, 9, 10, 11, 37, 52, 83, 90, 124, 141, 142) executed with a possibility of linear positioning movement and/or rotation and/or free linear movement; moreover, said adjustable pelvic belt (1, 47) and at least one said means (3, 51) for holding the thigh in a given position are connected to one another by the first connecting rod (8, 52) executed with a possibility of rotation and free linear movement, comprising the first module (A) executed with a possibility of positioning rotation in the horizontal plane and hip rotation in the static position and during movement; at least one said means (3, 51) for holding the thigh in a given position, at least one said means (4, 89) for rotating the tibia, and at least one said means (5, 121) for holding the tibia in a given position are connected to one another by the second and third rods (9,83, 10, 90), respectively, comprising the second module (B) wherein said second rod (9, 83) is executed with a possibility of rotation and linear positioning movement, said third rod (10, 90) is executed with a possibility of linear positioning movement, and said second module (B) is executed with a possibility of changing the position of the tibia by outer or inner rotation of the tibia in the horizontal plane and the correction of the position of the foot in the frontal plane; at least one said means (5, 121) for holding the tibia in a given position and at least one said means (6, 130) for correcting the position of the foot and the movement range thereof in the talocrural joint are connected to one another by the fourth rod (11, 124) executed with a possibility of linear positioning movement and comprise the third module (C) executed with a possibility of changing the position of the tibia and the foot by outer or inner rotation of the tibia and the foot in the horizontal plane; further, said first, second, and third modules (A, B, C) are executed with a possibility of independent use or in a given combination depending on the type of pathological configurations of the user's lower extremities.

2. Device of claim 1,
wherein said adjustable pelvic belt (1) contains supporting plate (12) on which base (13) is mounted that is oriented along the pelvic belt, on each of the opposing sides of which there is means (2) for centering the femoral head comprising flange (14) featuring a semi-spherical concavity, removable lid (15) firmly connected to said flange (14) and featuring an inverse semi-spherical concavity, and sphere shaped hinge (16) firmly secured in said concavities with a possibility of free positional rotation and featuring the first through channel in which, with a possibility of free movement, the first end of said first rod (8) is secured.

3. Device of claim 1,
wherein said means (3) for holding the thigh in a given position comprises the first and second parts (17, 18) positioned with a possibility of free rotation one relative to the other in the sagittal plane and with a possibility of positioning rotation in the horizontal plane; moreover, the device contains adjustable thigh cuff (19) on which, with a possibility of rotation in the sagittal plane, first part (17) of said means (3) for holding the thigh in a given position is fastened having the second through channel in which, with a possibility of rotation and linear positioning movement, the first end of said second rod (9) is positioned, and in the second part (18) of said means (3) for holding the thigh in a given position there is the third through channel in which, with a possibility of free linear movement, the second end of said first rod (8) is positioned.

4. Device of claim 3,
wherein said means (3) for holding the thigh in a given position contains axle (21) connecting said thigh cuff (19) with said first and second parts (17, 18) of means (3) for holding the thigh in a given position; moreover, the ends of this axle (21) are fastened with a possibility of free rotation on said adjustable thigh cuff (19) of the thigh and said second part (18) of means (3) for holding the thigh in a given position.

5. Device of claim 1,
wherein said means (4) for rotating the tibia comprises two parts (25, 26) positioned with a possibility of positioning rotation of one relative to the other in the frontal and horizontal planes; moreover, first part (25) of said means (4) for rotating the knee joint has the fourth through channel in which, with a possibility of linear positioning movement, the second end of said second rod (9) is secured, and second part (26) of said means (4) for rotating the tibia features slit (27) in which, on axle (28), knee hinge (29) is placed executed with a possibility of limiting flexion and extension of the tibia in the sagittal plane and having a socket in which the first end of said third rod (10) is firmly secured.

6. Device of claim 5,
wherein said knee hinge (29) contains needle bearing (30) the axle of which is secured, with its ends, at the opposing sides of said second part (26) of means (4) for rotating the tibia, and the region of said slit (27) in second part (26) features stop (31) limiting the turning of said knee hinge (29) in the sagittal plane.

7. Device of claim 5,
wherein said means (4) for rotating the tibia contains axle (28), one end of which is firmly secured in said first part (25) of means (4) for rotating the tibia, and the other end of said axle (28) is positioned in said second part (26) of means (4) for rotating the knee joint with a possibility of rotation of said second part (26) relative to its first part (25).

8. Device of claim 1,
wherein said means (5) for holding the tibia in a given position contains adjustable calf cuff (34) and base (35) having the fifth and sixth through channels in which, with a possibility of linear positioning movement, the second end of said third rod (10) and the first end of said fourth rod (11) are secured, respectively; moreover, said base (35) has axle (36) on which, with a possibility of rotation in the sagittal plane, said adjustable calf cuff (34) is secured.

9. Device of claim 1,
wherein said means (5) for holding the tibia in a given position contains first and second adjustable calf cuffs (341, 342) and first and second bases (351, 352), each of which has the seventh and eighth through channels; moreover, the device contains intermediate rod (37), and said seventh through channel of said first base (351) has a firmly secured second end of said third rod (10), whereas said eighth through channel of said first base (351) has, with a possibility of linear positioning movement, the secured first end of said intermediate rod (37), and in said seventh and eighth through channels of said second base (352), with a possibility of linear positioning movement, the second end of said intermediate rod (37) and the first end of said fourth rod (11) are secured, respectively, wherein each said base (351, 352) has axle (36) on which, with a possibility of rotation in the sagittal plane, the corresponding said adjustable calf cuff (341, 342) is secured.

10. Device of claim 9,
wherein said intermediate rod (37) is executed to be bent according to the shape of the user's tibia.

11. Device of claim 1,
wherein said means (6) for correcting the position of the foot and the movement range thereof in the talocrural joint contains talocrural hinge (38) having hollow body (39) in which tip (40) is placed, the first end of which has a firmly secured second end of said fourth rod (11), and the second end of said tip (40) is secured in said hollow body (39) on axle (41) of said talocrural hinge (38) with a possibility of rotation in the sagittal plane.

12. Device of claim 11,
wherein it contains connecting plate (43) with its one end secured on said axle (41) of said talocrural hinge (38) with a possibility of rotation in the sagittal plane, and its other end firmly attached to said means (7) for accommodating the foot.

13. Device of claim 12,
wherein the configuration of said connecting plate (43) conforms to the anatomical specifications of the user's foot.

14. Device of claim 11,
wherein at least one spring element (42) is placed in said hollow body (39) of talocrural hinge (38) of said means (6) for correcting the position of the foot and the movement range thereof in the talocrural joint, that is executed with a possibility to limit rotation of the foot in the sagittal plane.

15. Device of claim 1,
wherein said means (7) for accommodating the foot contains boot (44) and at least one fastening element (45) for holding the foot in a given position.

16. Device of claim 1,
wherein it contains means (46) for extending the knee joint that is fastened in the zone of the corresponding ends of said second and third rods (9, 10).

17. Device of claim 5,
wherein said means (46) for extending the knee joint contains at least one spring (461) whose one end is fastened to said second part (26) of means (4) for rotating the tibia, and its other end is fastened on said first end of third rod (10).

18. Device of claim 16,
wherein said means (46) for extending the knee joint contains at least one mover placed in the zone where the corresponding ends of said second and third rods (9, 10) are located.

19. Device of claim 1,
wherein it contains a mover fastened on said adjustable pelvic belt (1) in the zone where said means (2) for centering the femoral head is located.

20. Device of claim 1,
wherein said adjustable pelvic belt (47) contains base (48), near each of the opposing ends of which corresponding landing place (56) is located containing the first ring-shaped ridge surface, on which corresponding means (49) for centering the femoral head is placed that is fastened on the corresponding landing place (56) with a possibility of positional rotation and contains body (57) on the surface of which, facing base (48), there is the second ring-shaped ridge surface, and bevel-edged nut (58) positioned between said base (48) and said body (57) with a possibility of positioning rotation and having, on its butt-ends, the third and fourth ring-shaped ridge surfaces executed with a possibility of interlocking with said first and second ring-shaped ridge surfaces, respectively.

21. Device of claim 20,
wherein the device has at least one adjustable thigh cuff (50) that is executed with a possibility of rotation in the sagittal plane and on which, with a possibility of positioning rotation in the horizontal plane, corresponding means (51) for holding the thigh in a given position is fastened, and inside said body (57) of means (49) for centering the femoral head there is the ninth through channel oriented along the base, in which means (59) for fastening the first end of said first connecting rod (52) is secured, executed to allow free rotation and linear positioning movement of said first end of first connecting rod (52), said second end of which is positioned in said means (51) for holding the thigh in a given position.

22. Device of claim 21,
wherein said means (59) for fastening the first end of said first connecting rod (52) contains first and second inserts (67, 68) with corresponding flanges (69, 70), positioned with a possibility of free movement in said ninth through channel of said means (49) for centering the femoral head from the opposite ends; moreover, the outer surface of said first end of first rod (52) and inner surfaces of said first and second insert (67, 68) are threaded and comprise a threaded assembly to ensure linear positioning movement of said first end of first rod (52).

23. Device of claim 20,
wherein said bevel-edged nut (58) is executed with a possibility of discrete positioning rotation; moreover, there is scale (65) on the corresponding said landing place (56) around said first ring-shaped ridged surface, the unit of which corresponds to a step of the discrete positioning rotation of said bevel-edged nut (58).

24. Device of claim 23,
wherein the bevel angle of said bevel-edged nut (58) is from 3 to 30°.

25. Device of claim 20,
wherein said means for centering the femoral head (49) contains first flat spring (60) placed between juxtaposed said surfaces of said base (48) and bevel-edged nut (58), respectively, inside said first and third ring-shaped ridged surfaces.

26. Device of claim 20,
wherein said means for centering the femoral head (49) contains second flat spring (61) placed between juxtaposed said surfaces of body (57) and bevel-edged nut (58), respectively, inside said second and fourth shaped ridged surfaces.

27. Device of claim 21,
wherein said means (51) for holding the thigh in a given position contains hollow body (71) and unit (72) of fastening said means (51) for holding the thigh in a given position to said adjustable thigh cuff (50); moreover, said unit (72) is fastened from one side of this hollow body (71) partially inside of it with a possibility of rotating the thigh in a static position and during movement, and said second end of first rod (52) is positioned from the opposite side of said hollow body (71) with a possibility of linear movements.

28. Device of claim 27,
wherein said unit (72) of fastening the means for holding the thigh in a given position contains insert (78) fastened in said hollow body (71) of means (51) for holding the thigh in a given position, and having tailpiece (79) protruding from this hollow body (71) in which a ball bearing is placed having stator (80) and rotor (81), executed with a possibility of rotation in the sagittal and horizontal planes.

29. Device of claim 1,
wherein it contains at least one unit (84) of fastening the first end of said second rod (83) positioned with a possibility of rotation in the horizontal plane and having the tenth through channel in which, with a possibility of linear positioning movement, said first end of second rod (83) is secured.

30. Device of claim 1,
wherein said means (89) for rotating the tibia contains stepped body (91) in the first step of which the second end of said second rod (83) is fastened, that is executed with a possibility of positioning rotation in the frontal and horizontal planes, and in the second step of which knee hinge (92) is mounted that is executed with a possibility of limited rotation in the sagittal plane, and there is unit (94) of fastening the first end of said third rod (90) connected to said knee hinge (92).

31. Device of claim 30,
wherein said knee hinge (92) contains base (96), lid (97) executed with a possibility of discrete positioning rotation and fixation in a given position, spring (98) with its one end fastened in said second step of stepped body (91) and the other—in said lid (97) of knee hinge (92), and axle (100) whose one end is fastened in said second step of stepped body (91) and the other—in said lid (97) of knee hinge (92).

32. Device of claim 29,
wherein insert (95) is positioned between said base (96) of knee hinge (92) and said second step of stepped body (91), executed with a possibility of limiting rotation of said knee hinge.

33. Device of claim 32,
wherein said insert (95) is C-shaped and made of a resilient material.

34. Device of claim 30,
wherein said unit (94) of fastening the first end of third rod (90) contains collar (104) fastened on said base (96) of knee hinge (92), and lock (105) executed with a possibility of entering inter-engagement with said lid (97) of knee hinge (92).

35. Device of claim 34,
wherein it contains clamping element (107) grasping said collar (104) and lock (105).

36. Device of claim 1,
wherein said means (89) for rotating the tibia contains a ridged pair executed with a possibility of limited rotation in the sagittal plane and comprising first and second gears (108, 109), each of which has ridged crown (108$_1$, 109$_1$) and rotation axle (110, 111), first and second side plates (112) positioned from the butt-end of the ridged pair in which first and second rotation axles (110, 111) are fastened that pass through said first and second gears (108, 109), and front and back stops (113, 114) fastened on one of said side plates (112), wherein said second end of second rod (83) is fastened in said first gear (108), and said first end of third rod (90) is fastened in said second gear (109).

37. Device of claim 1,
wherein said means (121) for holding the tibia in a given position contains first adjustable calf cuff (122$_1$) on which, with a possibility of rotation in the sagittal plane, first base (123) is fastened, and second adjustable calf cuff (122$_2$) on which, with a possibility of rotation in the sagittal plane, second base (123) is fastened; moreover, the device contains first intermediate rod (141) connecting said first and second adjustable calf cuffs (122$_1$, 122$_2$).

38. Device of claim 1,
wherein said means (130) for correcting the position of the foot and the movement range thereof in the talocrural joint contains outer talocrural hinge (131) having hollow body (133) in which tip (134) is inserted on whose one end the second end of said fourth rod (124) is fastened, and the other end of said tip (124) is fastened on axle (132) of outer talocrural hinge (131) with a possibility of rotation in the sagittal plane; moreover, the device contains bent connecting plate (135) with its one end fastened to said axle (132) of outer talocrural hinge (131) with a possibility of rotation in the sagittal plane, and the other end fastened to said means for accommodating the foot.

39. Device of claim 38,
wherein at least one resilient element (137) is installed in said hollow body (133) of means (130) for correcting the position of the foot and the movement range thereof in the talocrural joint, executed with a possibility of limiting rotation of the foot in the sagittal plane.

40. Device of claim 1,
wherein said means (130) for correcting the position of the foot and the movement range thereof in the talocrural joint contains outer talocrural hinge (131) having axle (132) and body (133) in which the second end of said fourth rod (124) is fastened; moreover, the device contains bent connecting plate (135) that is spring-loaded to said body (133), with its one end fastened to said axle (132) of outer talocrural joint (131) with a possibility of rotation in the sagittal plane, and the other end—to said means for accommodating the foot.

41. Device of claim 36,
wherein it contains at least one second intermediate rod (142), and said means (130) for correcting the position of the foot and the movement range thereof, in the talocrural joint contains at least one inner talocrural hinge (145); moreover, first and second collars (143) are placed onto said first and second adjustable calf cuffs (122$_1$, 122$_2$) from the inner surface of the calf with a possibility of rotation in the sagittal plane, and in the first collar, with a possibility of linear positioning movements, the first end of said second intermediate rod (142) is fastened, the second end of which is passed through said second collar (143) and connected to said inner talocrural hinge (145).

42. Device of claim 39,
wherein said inner talocrural hinge (145) has hollow body in which a tip is installed, on one end of which said second end of the second intermediate rod is fastened, and the second end of the tip is fastened on the axle of said inner talocrural hinge with a possibility of rotation in the sagittal plane; moreover, the device contains a bent connecting plate whose one end is fastened to the axle of said inner talocrural hinge with a possibility of rotation in the sagittal plane, and the other end is fastened to said means for accommodating the foot.

43. Device of claim 39,
wherein said inner talocrural hinge (145) has a body in which said second end of the second intermediate rod is fastened; moreover, the device contains a bent connecting plate spring-loaded to said body, with its one end fastened to the axle of said inner talocrural hinge with a possibility of rotation in the sagittal plane, and its other end fastened to said means for accommodating the foot.

44. Device of claim 1,
wherein each said first rod is executed as a cylindrical pivot with a complex three-dimensional shape and has its first straight-line segment (8$_1$, 53) oriented along the rotation axis of said first rod (8, 52), its second straight-line segment (8$_2$, 54) essentially oriented along the user's tibia, and its third curvilinear segment (8$_3$, 55) smoothly connecting said first straight-line segment (8$_1$, 53) and second straight-line segment (8$_2$, 54).

45. Method for correcting pathological configurations of segments of the lower extremities including correction of pathological configurations of segments of at least one lower extremity with the aid of an orthopedic device, wherein
said correction of said pathological configurations of said segments of the corresponding lower extremity is carried out by means of the correction of the position of longitudinal axes of said segments of the corresponding lower extremity in the horizontal and/or frontal and/or sagittal planes,
further, said correction of the position of said longitudinal axes comprises:
dosed elimination of the imbalance of forces in the muscles supporting the corresponding joints of said segments of the corresponding lower extremity;
subsequent fixation of said segments in the corrected position of said longitudinal axes of said segments of the corresponding lower extremity in the horizontal and/or frontal and/or sagittal planes;
execution of said subsequent fixation using said orthopedic device comprising at least one module of a modular exoskeleton fitted for individual adjustment that brings said corrected position of said longitudinal axes of said segments closer to the physiologically correct position of these axes;
execution of said subsequent fixation of said segments in said corrected position of said longitudinal axes with a possibility of movements in the corresponding joints of said segments of the corresponding lower extremity around the rotation axes of these joints within a predetermined range defined by, at minimum, one module of said modular exoskeleton;
execution of said subsequent fixation of said segments in said corrected position of said longitudinal axes enabling the stereotype of the user's movements in the corresponding joints of said segments of the corresponding lower extremity to be brought closer to the physiologically correct movement stereotype.

46. Method of claim 45, wherein
in the capacity of said pathological configurations of said segments, hip adduction in the corresponding hip joint is reduced;
in the capacity of said correction of said adduction of said hip in the corresponding hip joint, the position of the longitudinal axis of said hip in the frontal plane is corrected;
in the capacity of said dosed elimination of the imbalance of forces in the muscles supporting the corresponding joints, dosed extension of adductors of said hip and dosed correction of the position of the femoral head of said hip in the acetabulum of the corresponding hip joint by means of dosed abduction of said hip in said frontal plane are carried out;

in the capacity of said subsequent fixation of said segments in said corrected position of said longitudinal axes, fixation of the corrected position of said hip in the corresponding hip joint of the corresponding lower extremity in said corrected position of said longitudinal axis of said hip of the corresponding lower extremity in said frontal plane is carried out;

said fixation of the corrected position of said hip in the corresponding hip joint is carried out using the first module of said modular exoskeleton fitted for performing movements in the corresponding hip joint in the horizontal, frontal, and sagittal planes within a predetermined range defined by said first module of said modular exoskeleton;

said fixation of the corrected position of said hip in the corresponding hip joint is carried out with a possibility of bringing the stereotype of the user's movements in the corresponding hip joint closer to the physiologically correct movement stereotype.

47. Method of claim 46, wherein simultaneously with said dosed abduction of said hip in said frontal plane, dosed outer rotation of said hip in said horizontal plane is carried out.

48. Method of claim 45, wherein in the capacity of said pathological configurations of said segments, inner rotation of the corresponding lower extremity is reduced;

in the capacity of said correction of said inner rotation of the corresponding lower extremity, correction of the position of the longitudinal axis of the corresponding lower extremity in said horizontal plane is carried out;

in the capacity of said dosed elimination of the imbalance of forces in the muscles supporting the corresponding joints, dosed elimination of the imbalance of forces in the muscles supporting the corresponding hip joint as well as outer rotation of the lower extremity in the corresponding hip joint are carried out;

in the capacity of said subsequent fixation of said segments in said corrected position of said longitudinal axes, fixation of the corrected position of the corresponding lower extremity in said corrected position of said longitudinal axis of the corresponding lower extremity in said horizontal plane is carried out;

said fixation of the corrected position of the corresponding lower extremity is carried out using the first and the second modules of said modular exoskeleton fitted for performing movements in the corresponding hip joint in the horizontal plane within a predetermined range defined by said first and second modules of said modular exoskeleton;

said fixation of the corrected position of the corresponding lower extremity is carried out with a possibility of bringing the stereotype of the user's movements in the corresponding hip joint closer to the physiologically correct movement stereotype.

49. Method of claim 45, wherein in the capacity of said pathological configurations of said segments, recurvation of the tibia in the knee joint of the corresponding lower extremity is reduced;

in the capacity of said correction of said recurvation of said tibia in said knee joint of the corresponding lower extremity, correction of the position of the longitudinal axis of the corresponding lower extremity in said sagittal plane is carried out;

in the capacity of said dosed elimination of the imbalance of forces in the muscles supporting the corresponding joints, dosed reduction of said tibia's extension in said knee joint of the corresponding lower extremity in the sagittal plane is carried out during the support period upon locomotion;

in the capacity of said subsequent fixation of said segments in said corrected position of said longitudinal axes, fixation of the corrected position of the corresponding lower extremity in said corrected position of said longitudinal axis of the corresponding lower extremity in said sagittal plane is carried out;

said fixation of the corrected position of the corresponding lower extremity is carried out using the second module of said modular exoskeleton fitted for flexion and extension of said tibia in said knee joint of the corresponding lower extremity in said sagittal plane within a predetermined range defined by said second module of said modular exoskeleton;

said fixation of the corrected position of the corresponding lower extremity is carried out with a possibility of bringing the stereotype of the user's movements in said knee joint closer to the physiologically correct movement stereotype.

50. Method of claim 45, wherein in the capacity of said pathological configurations of said segments, flexion of the tibia in the knee joint of the corresponding lower extremity is reduced;

in the capacity of said correction of said flexion of said tibia in said knee joint of the corresponding lower extremity, correction of the position of the longitudinal axis of the corresponding lower extremity in said sagittal plane is carried out;

in the capacity of said dosed elimination of the imbalance of forces in the muscles supporting the corresponding joints, dosed elimination of the imbalance of forces supporting said knee joint of the corresponding lower extremity as well as reduction of said tibia's flexion in said knee joint of the corresponding lower extremity in the sagittal plane during the support period upon locomotion are carried out;

in the capacity of said subsequent fixation of said segments in said corrected position of said longitudinal axes, fixation of the corrected position of the corresponding lower extremity in said corrected position of said longitudinal axis of the corresponding lower extremity in said sagittal plane is carried out;

said fixation of the corrected position of the corresponding lower extremity is carried out using the spring-assisted second module of said modular exoskeleton fitted for flexion and extension of said tibia in said knee joint of the corresponding lower extremity in said sagittal plane within a predetermined range defined by said spring-assisted second module of said modular exoskeleton;

said fixation of the corrected position of the corresponding lower extremity is carried out with a possibility of bringing the stereotype of the user's movements in said knee joint closer to the physiologically correct movement stereotype.

51. Method of claim 45, wherein in the capacity of said pathological configurations of said segments, varus or valgus positioning of the tibia in the knee joint of the corresponding lower extremity is reduced;

in the capacity of said correction of said varus or valgus positioning of said tibia in said knee joint of the corresponding lower extremity, correction of the position of the longitudinal axis of the corresponding lower extremity in said frontal plane is carried out;

in the capacity of said dosed elimination of the imbalance of forces in the muscles supporting the corresponding joints, dosed elimination of the imbalance of forces supporting said knee joint of the corresponding lower extremity as well as correction of the position of said tibia of the corresponding lower extremity in said frontal plane are carried out;

in the capacity of said subsequent fixation of said segments in said corrected position of said longitudinal axes, fixation of the corrected position of the corresponding lower extremity in said corrected position of said longitudinal axis of the corresponding lower extremity in said frontal plane is carried out;

said fixation of the corrected position of the corresponding lower extremity is carried out using the second module of said modular exoskeleton fitted for flexion and extension of said tibia in said knee joint of the corresponding lower extremity in said sagittal plane within a predetermined range defined by said second module of said modular exoskeleton;

said fixation of the corrected position of the corresponding lower extremity is carried out with a possibility of bringing the stereotype of the user's movements in said knee joint closer to the physiologically correct movement stereotype.

52. Method of claim 45, wherein in the capacity of said pathological configurations of said segments, foot adduction or abduction in the talocrural joint of the corresponding lower extremity is reduced;

in the capacity of said correction of said foot adduction or abduction in said talocrural joint of the corresponding lower extremity, correction of the position of the longitudinal axis of said talocrural joint of the corresponding lower extremity in said horizontal plane is carried out;

in the capacity of said dosed elimination of the imbalance of forces in the muscles supporting the corresponding joints, dosed elimination of the imbalance of forces supporting said talocrural joint as well as the corresponding abduction or adduction of said foot in said horizontal plane are carried out;

in the capacity of said subsequent fixation of said segments in said corrected position of said longitudinal axes, fixation of the corrected position of said talocrural joint of the corresponding lower extremity in said corrected position of said longitudinal axis of said talocrural joint of the corresponding lower extremity in said horizontal plane is carried out;

said fixation of the corrected position of said talocrural joint of the corresponding lower extremity is carried out using the third module of said modular exoskeleton fitted for plantar flexion and dorsiflexion of said foot in said talocrural joint of the corresponding lower extremity in said sagittal plane within a predetermined range defined by said third module of said modular exoskeleton;

said fixation of the corrected position of the corresponding lower extremity is carried out with a possibility of bringing the stereotype of the user's movements in said talocrural joint closer to the physiologically correct movement stereotype.

53. Method of claim 45, wherein in the capacity of said pathological configurations of said segments, varus or valgus positioning of the foot in the talocrural joint of the corresponding lower extremity is reduced;

in the capacity of said correction of said varus or valgus positioning of said foot in said talocrural joint of the corresponding lower extremity, correction of the position of the longitudinal axis of said talocrural joint of the corresponding lower extremity in said frontal plane is carried out;

in the capacity of said dosed elimination of the imbalance of forces in the muscles supporting the corresponding joints, dosed elimination of the imbalance of forces of the muscles of the calf as well as change of the position of said foot in said talocrural joint in said frontal plane are carried out;

in the capacity of said subsequent fixation of said segments in said corrected position of said longitudinal axes, fixation of the corrected position of said foot in said talocrural joint of the corresponding lower extremity in said corrected position of said longitudinal axis of said talocrural joint of the corresponding lower extremity in said frontal plane is carried out;

said fixation of the corrected position of said foot in said talocrural joint of the corresponding lower extremity is carried out using the third module of said modular exoskeleton and means for accommodating said foot of said modular exoskeleton fitted for plantar flexion and dorsiflexion of said foot in said talocrural joint of the corresponding lower extremity in said sagittal plane within a predetermined range defined by said third module and said means for accommodating said foot of said modular exoskeleton;

said fixation of the corrected position of the corresponding lower extremity is carried out with a possibility of bringing the stereotype of the user's movements in said talocrural joint closer to the physiologically correct movement stereotype.

54. Method of claim 45, wherein in the capacity of said pathological configurations of said segments, dropping of the foot in the talocrural joint of the corresponding lower extremity is reduced;

in the capacity of said correction of said dropping of said foot in said talocrural joint of the corresponding lower extremity, correction of the position of the longitudinal axis of said talocrural joint of the corresponding lower extremity in said sagittal plane is carried out;

in the capacity of said dosed elimination of the imbalance of forces in the muscles supporting the corresponding joints, reduction of dorsiflexion of said foot in said talocrural joint in said sagittal plane is carried out;

in the capacity of said subsequent fixation of said segments in said corrected position of said longitudinal axes, fixation of the corrected position of said talocrural joint of the corresponding lower extremity in said corrected position of said longitudinal axis of said talocrural joint of the corresponding lower extremity in said sagittal plane is carried out;

said fixation of the corrected position of said talocrural joint of the corresponding lower extremity is carried out using the third module of said modular exoskeleton fitted for dorsiflexion of said foot in said talocrural joint of the corresponding lower extremity in said sagittal plane within a predetermined range defined by said third module of said modular exoskeleton;

said fixation of the corrected position of the corresponding lower extremity is carried out with a possibility of bringing the stereotype of the user's movements in said talocrural joint closer to the physiologically correct movement stereotype.

55. Method of claim 45, wherein in the capacity of said pathological configurations of said segments, equine positioning of the foot in the talocrural joint of the corresponding lower extremity is reduced;

in the capacity of said correction of said equine positioning of said foot in said talocrural joint of the corresponding lower extremity, correction of the position of the longitudinal axis of said talocrural joint of the corresponding lower extremity in said sagittal plane is carried out;

in the capacity of said dosed elimination of the imbalance of forces in the muscles supporting the corresponding joints, dosed stretching of the triceps muscle of the corresponding calf and reduction of dorsiflexion of said foot in said talocrural joint in said sagittal plane are carried out;

in the capacity of said subsequent fixation of said segments in said corrected position of said longitudinal axes, fixation of the corrected position of said talocrural joint of the corresponding lower extremity in said corrected position of said longitudinal axis of said talocrural joint of the corresponding lower extremity in said sagittal plane is carried out;

said fixation of the corrected position of said talocrural joint of the corresponding lower extremity is carried out using the third module of said modular exoskeleton fitted for dorsiflexion of said foot in said talocrural joint of the corresponding lower extremity in said sagittal plane within a predetermined range defined by said third module of said modular exoskeleton;

said fixation of the corrected position of the corresponding lower extremity is carried out with a possibility of bringing the stereotype of the user's movements in said talocrural joint closer to the physiologically correct movement stereotype.

56. Method of claim 45, wherein said pathological configurations of segments of two lower extremities are reduced, their correction being achieved independently for each said lower extremity without cross-effect.

57. Method of claim 45, wherein said correction of said pathological configurations of said segments of the corresponding lower extremity is carried out in the range that precludes the user's experiencing painful sensations.

58. Method of claim 45, wherein said correction of said pathological configurations of said segments of the corresponding lower extremity is carried out until the physiologically correct position of the longitudinal axis of the corresponding lower extremity of the user is achieved in the position "standing."

59. Method of claim 45, wherein following said correction of said pathological configurations of said segments of the corresponding lower extremity, active dynamic exercises are performed to eliminate functional deficiency in the corresponding muscles and/or influences are exerted on the user that are chosen from a set comprising manual, device-mediated, physical therapy, and medicinal options, alone or in combinations.

* * * * *